(12) United States Patent
Linker, III et al.

(10) Patent No.: US 7,344,525 B2
(45) Date of Patent: Mar. 18, 2008

(54) ABSORBENT ARTICLE WITH IMPROVED FASTENING SYSTEM

(75) Inventors: Paul Means Linker, III, Appleton, WI (US); Duane Girard Uitenbroek, Little Chute, WI (US); Thomas Harold Roessler, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 479 days.

(21) Appl. No.: 10/302,429

(22) Filed: Nov. 22, 2002

(65) Prior Publication Data

US 2004/0102745 A1    May 27, 2004

(51) Int. Cl.
*A61F 13/15*    (2006.01)
(52) U.S. Cl. .................. 604/391; 604/389; 604/387; 604/394; 604/396
(58) Field of Classification Search ............. 24/445, 24/446, 449–452, 455; 604/358–402
See application file for complete search history.

(56) References Cited

U.S. PATENT DOCUMENTS

| | | | |
|---|---|---|---|
| 4,663,220 A | 5/1987 | Wisneski et al. | |
| 4,704,116 A | 11/1987 | Enloe | |
| 4,798,603 A | 1/1989 | Meyer et al. | |
| 4,894,060 A * | 1/1990 | Nestegard | 604/391 |
| 5,176,668 A | 1/1993 | Bernardin | |
| 5,192,606 A | 3/1993 | Proxmire et al. | |
| 5,226,992 A | 7/1993 | Morman | |
| 5,326,415 A | 7/1994 | Thomas et al. | |
| 5,336,545 A | 8/1994 | Morman | |
| 5,369,853 A * | 12/1994 | Okawa et al. | 24/446 |
| 5,509,915 A | 4/1996 | Hanson et al. | |
| 5,515,583 A * | 5/1996 | Higashinaka | 24/446 |
| 5,622,578 A * | 4/1997 | Thomas | 156/66 |
| 5,692,271 A * | 12/1997 | Provost et al. | 24/452 |
| 5,695,868 A | 12/1997 | McCormack | |
| 5,720,740 A * | 2/1998 | Thomas | 604/391 |
| 5,745,961 A * | 5/1998 | Okawa et al. | 24/446 |
| 5,782,819 A | 7/1998 | Tanzer et al. | |
| 5,789,065 A | 8/1998 | Haffner et al. | |
| 5,843,056 A | 12/1998 | Good et al. | |
| 5,858,515 A | 1/1999 | Stokes et al. | |
| 5,928,212 A * | 7/1999 | Kline et al. | 604/391 |

(Continued)

FOREIGN PATENT DOCUMENTS

EP    0 217 032 B1    2/1992

(Continued)

*Primary Examiner*—Jacqueline F. Stephens
(74) *Attorney, Agent, or Firm*—Alyssa Dudkowski; David J. Arteman

(57) ABSTRACT

An absorbent article includes a pair of front ear regions as part of a front waist region, a pair of back ear portions including a mechanical fastener as part of a back waist region, a crotch region connecting the front waist region and the back waist region, and a landing zone including a base material and a first discrete fastener element group embedded in the base material. The first discrete fastener element group includes at least one first discrete fastener element having a profile height. The base material has a profile height that is greater than the profile height of the first discrete fastener element. The landing zone may be associated with the outer cover in the front waist region between the front ear regions.

11 Claims, 11 Drawing Sheets

U.S. PATENT DOCUMENTS

| | | | |
|---|---|---|---|
| 5,983,467 A | 11/1999 | Duffy | |
| 6,061,881 A * | 5/2000 | Takizawa et al. | 24/446 |
| 6,099,516 A * | 8/2000 | Pozniak et al. | 604/386 |
| 6,149,934 A | 11/2000 | Krzysik et al. | |
| 6,276,032 B1 * | 8/2001 | Nortman et al. | 24/572.1 |
| 6,478,784 B1 * | 11/2002 | Johnson et al. | 604/385.01 |
| 6,489,004 B1 | 12/2002 | Martin et al. | |
| 6,648,866 B2 * | 11/2003 | Magee et al. | 604/385.03 |

FOREIGN PATENT DOCUMENTS

| | | |
|---|---|---|
| EP | 0 832 573 B1 | 6/2002 |
| WO | WO 9312687 A1 * | 7/1993 |
| WO | WO 00/50229 A1 | 8/2000 |
| WO | WO 01/43684 A1 | 6/2001 |
| WO | WO 01/67912 A2 | 9/2001 |

* cited by examiner

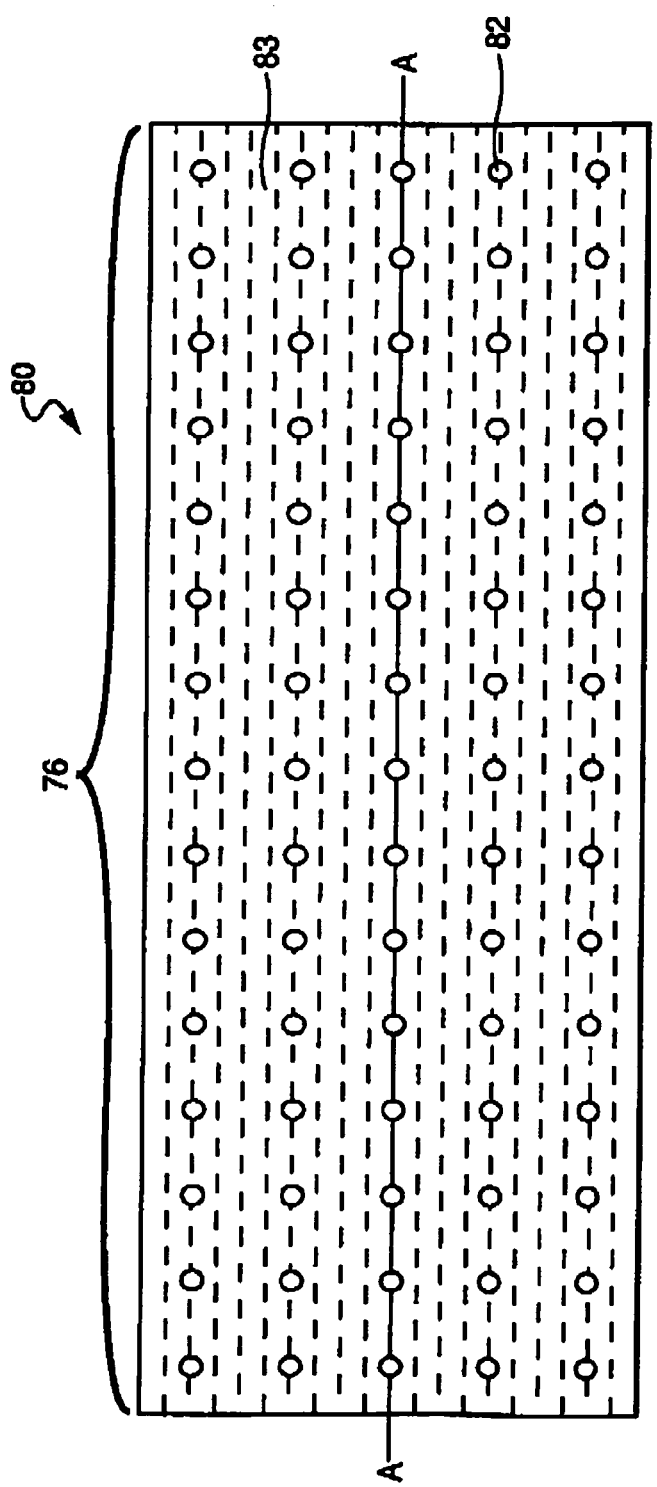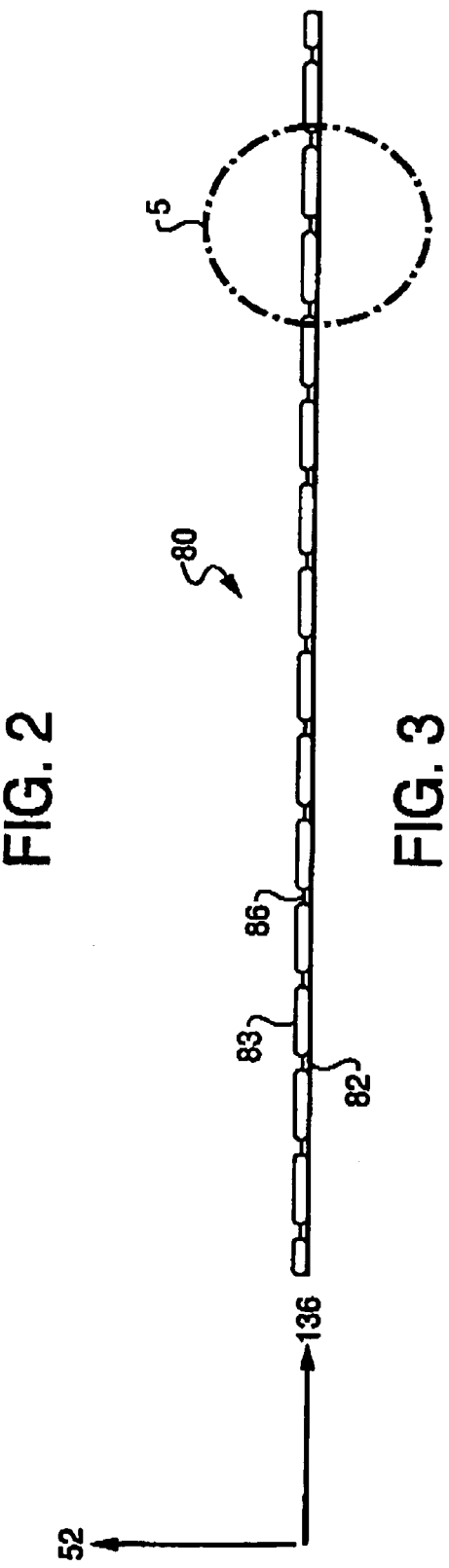
FIG. 2
FIG. 3

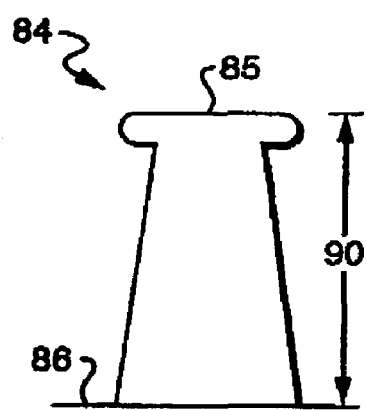
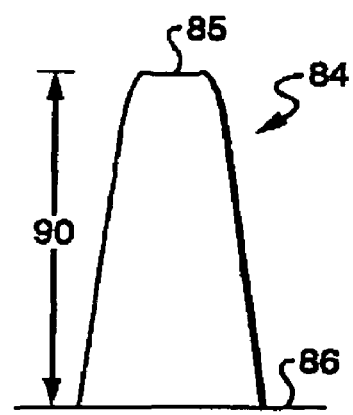
FIG. 11     FIG. 12
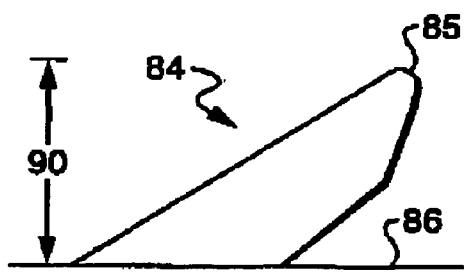
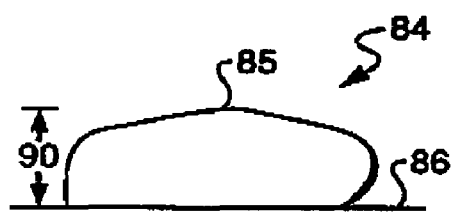
FIG. 13     FIG. 14
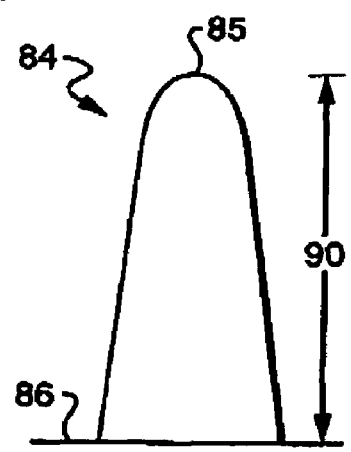
FIG. 15

ABSORBENT ARTICLE WITH IMPROVED FASTENING SYSTEM

BACKGROUND OF THE INVENTION

The present invention relates to a fastening system suitable for use on absorbent articles. More particularly, the present invention relates to absorbent articles having improved fit and stability of closure provided by the fastening system.

Absorbent articles such as diapers, training pants or incontinence garments desirably provide a close, comfortable fit about the wearer and contain body exudates. Disposable absorbent articles can be secured about the wearer by a variety of fastening systems. Conventional diapers have typically included a front waist portion and a back waist portion that are releasably connected about the hips of the wearer during use by conventional fastening systems such as adhesive tape fasteners or hook and loop fasteners. For example, conventional fastening systems typically include a pair of fasteners, such as hook tabs, located on the outermost corners of the diaper in the back waist region of the diaper and a complimentary fastener, such as a loop panel, located on the exterior surface of the outer cover of the diaper in the front waist portion of the diaper. Typically, when a user dons the article, the hook tabs and the back waist region are lapped over the front waist portion of the article and the hook tabs are secured to the loop panel. The overlapping front and rear waist regions are in surface-to-surface contact and create the waist opening. Because the waist opening is typically formed by the union of the front waist portion and the back waist portion, the fastening system used to form that union may impact the fit of the absorbent article.

Once the article is being worn, the quality of the fit at the waist opening is a primary driver of the fit of the whole article. Just like the elastic waistband of the cloth underwear, the fit of the waist opening keeps the absorbent article from falling down. If an absorbent article begins to droop or sag during wear, the performance of the article may be compromised. More specifically, the article may leak.

The performance and containment of the absorbent article is typically improved by providing tension around the waist opening of the article and also by providing tension around the leg openings of the absorbent article through the addition of extensible materials to the product. Such conventional diapers have tension around the waist of the user and tension around the leg of the user when initially donned. It is desirable for an absorbent article to maintain its initial fastened position during use so as to maintain proper tension and ultimately proper fit. It is also desirable for absorbent articles to resist radial shifting in the fastener overlap region in the front portion of article so as to maintain both the leg tension and the waist tension. In various types of garments, such as a disposable diaper, the secured together portions of the garment, particularly in the fastener overlap region, are placed under tension. The tension in the fastening system results primarily from shear forces, both from the material elasticity and from user movements. The shear forces act to pull the fastening system apart in a direction essentially planer to the interface between the back fastener and the front fastener. Therefore, improvements in shear strength can improve fastening performance and in turn improve fit by reducing slippage and radial shifting due to the shear forces in the fastener overlap region. However, increased shear strength can also result in increased peel strength. The peel strength is a measure of the force required to pull (or peel) the back fastener away from the front fastener in a non-parallel direction. This force is felt by the user when removing the back fasteners from the front fasteners. Excessive peel strength can result in user dissatisfaction due to fasteners that are difficult to open.

Traditional absorbent products have not been optimized to resist radial shifting and shear slippage while maintaining acceptable peel strengths. The front waist portion of an absorbent article is generally flexible for comfort and fit. Also, the materials that make up the front and rear waist portions of absorbent articles have relatively low coefficients of friction when in surface-to-surface contact with one another. The result in traditional absorbent articles is that the leg elastic tension may pull down the front waist portion of the article causing radial shifting of the front waist portion of the article with respect to the rear waist portion of the article in the overlap section or slippage due to shear forces. This shifting and slippage may result in an undesirable loss of tension in both the waist opening and the leg portions of the absorbent garment. The loss of tension may also lead to reduction in the containment and performance of the article. The radial shifting may be worsened when the user attaches the tabs near the center of the front waist portion of the article thus increasing the amount of overlap between the front and rear waist portions of the absorbent article.

There exists a need for a fastening system that can reliably maintain the proper relationship between the rear and front waist portions and thereby maintain proper fit and tension in absorbent articles during use. There is also a need for a fastening system that can reduce radial shifting and shear slippage between the back and front waist regions while maintaining desirable peel strength. There is also a need for a fastening system that is gentle to the skin and does not cause red marking or discomfort during use.

SUMMARY OF THE INVENTION

In response to the difficulties and problems discussed above, new mechanical fastening systems have been discovered. The present invention is related to mechanical fastening systems that include a landing zone and to systems that may fasten directly into the outer cover. The landing zone may perform multiple functions. The landing zone of a fastening system typically performs a single function: the landing zone acts as the area of an absorbent article into which it is desirable to engage fasteners. With the mechanical fastening systems of the present invention, the landing zone may be configured to not only engage fasteners but to also increase the shear resistance and coefficient of friction of the landing zone. The increased friction and shear resistance may decrease radial shifting of the back waist portion relative to the front waist portion of an absorbent article and in turn maintain the initial fastening position.

The landing zone may include a base material and a plurality of discrete fastener elements. The discrete fastener elements may be embedded in the base material of the landing zone and in one aspect of the present invention, the base material of the landing zone includes a loop material. The loop material may include a backing material and a layer of a nonwoven spunbond web attached to the backing material. The nonwoven spunbond web may include a plurality of spunbond fibers or filaments formed to define a plurality of intertwined loop springs. Further, in another aspect of the present invention, the discrete fastener elements may be formed of thermoplastic polymers such as METALLOCENE, PEBAX, KRATON, polyethylene, polypropylene, polyurethane, polystyrene, polycarbonate, polyester, ethylene vinyl acetate, ethylene vinyl alcohol, ethylene vinyl acetate acrylate, or ethylene acrylic acid copolymers.

In yet another aspect, the discrete fastener elements may be embedded directly into the outer cover or liner to increase the coefficient of friction and shear resistance of the outer cover and liner respectively.

One aspect of the present invention relates to a disposable absorbent article. The disposable absorbent article may include an absorbent core located between an outer cover and a bodyside liner. The absorbent article may include a front waist region, a back waist region and a crotch region connecting the front and back waist regions. The front waist region may include front ear regions and the back waist region may include back ear portions. The back ear portions may further include a mechanical fastener. The absorbent article may include a landing zone associated with the outer cover of the absorbent article in the front waist region between the front ear regions. The landing zone may include a base material and a first discrete fastener element group embedded in the base material. The first discrete fastener element group may include at least one first discrete fastener element. The first discrete fastener element may be embedded in the base material of the landing zone and may be configured to increase the shear resistance of the landing zone. The mechanical fastener may be located on the outer cover or the body side liner and may be positioned to bring the back waist region in communication with the front waist region when the absorbent article is applied. The mechanical fastener may be configured to refasten ably engage the base material of the landing zone. The discrete fastener elements embedded in the base material may be configured to increase the shear resistance and coefficient of friction between the landing zone and the back ear portions. The increased coefficient of friction and increased shear resistance may reduce relative surface-to-surface and radial movement of the front waist region relative to the back waist region and help maintain the initial fastened position of the absorbent article.

Together, the mechanical fastener and the landing zone are configured to refasten ably secure the disposable absorbent article about a wearer. In one aspect of the invention, the base material of the landing zone may include a loop material and the mechanical fastener may include hook material. In another aspect, the base material may include a hook material and the mechanical fastener may include a loop material. The absorbent article may also include ear portions extending laterally outward from the back waist region. The back ear portions may be extendible. The back ear portions may include a fastening material and a may include a flexible layer. The fastening material may include a hook material that is refasten ably engageable with the base material of the landing zone.

The discrete fastener elements may be geometrically dispersed throughout the base material of the landing zone or may be concentrated in different areas to improve performance or fit. The absorbent article may also include additional discrete fastener element groups embedded in the outer cover in the front ear regions, embedded in the liner in the back ear portions, embedded in the flexible material of the mechanical fasteners, or combinations thereof. Each additional discrete fastener element group includes at least one discrete fastener element. The discrete fastener elements embedded in the landing zone and the discrete fastener elements embedded in the outer cover may have a lower profile height than the profile height of the base material of the landing zone or the outer cover respectively.

In other aspects, the discrete fastener elements may have circular, rectangular, oval, or irregular cross-sectional shapes. The discrete fastener elements may also be in the shape of lines. The discrete fastener elements may have the same cross-sectional shapes within a particular discrete fastener element group or may include various cross-sectional shapes within the same discrete fastener element group. The discrete fastener elements may have the same cross-sectional shapes from group to group or one or more discrete fastener element groups may include discrete fastener elements with different cross-sectional shapes.

The discrete fastener elements may also have one or more protrusions extending from a garment-facing surface of the discrete fastener elements to increase shear resistance and coefficient of friction. The protrusions may be shaped in the form of fingers, fins, nail heads, cones, blobs, mushrooms, fishhooks, or palm trees. All the discrete fastener elements of a discrete fastener element group may have protrusions or only some may have protrusions. The discrete fastener elements of a discrete fastener element group may have all the same shaped protrusions or may have more than one shaped protrusion within the same discrete fastener element group. The protrusion shape of the discrete fastener elements of one discrete fastener element group may be different than the protrusion shape of the discrete fastener elements of a different discrete fastener elements group. The protrusions may be configured to increase the shear resistance of the landing zone, the outer cover, the liner, the flexible layer or combinations thereof. Some or all of the protrusions throughout the absorbent article may be flexible or rigid.

For example, the landing zone of the absorbent article may include multiple discrete fastener element groups. Within one element group on the landing zone, there may be a mixture of discrete fastener elements, some elements having a circular cross-sectional shape and some elements having an oval cross-sectional shape. Another element group on the landing zone may include linear discrete fastener elements. Likewise, the liner material of the back ear portions may include one or more discrete fastener element groups. As with the landing zone, each discrete fastener element group on the liner material may have a mixture of discrete fastener elements of different cross-sectional shapes. Further, there may be differences in the cross-sectional shapes of the discrete fastener elements between the discrete fastener element groups. Each of the fastener element groups on the landing zone and the liner material may have discrete fastening elements having protrusions of various shapes.

In another aspect of the present invention the absorbent article that may include an outer cover, a bodyside liner and an absorbent core located between the outer cover and the bodyside liner. The absorbent article may also include a front waist region, a back waist region and a crotch region connecting the front waist region and the back waist region. The front waist region may include front ear regions and the back waist region may include back ear portions. The back ear portions may further include a mechanical fastener. The mechanical fastener may include a fastening material and may also include a flexible layer. The absorbent article may include a group of discrete fastener elements embedded in the outer cover of the absorbent article in the front waist region.

The discrete fastener element group may include at least one discrete fastener element. The discrete fastener elements may be configured to increase the shear resistance of the outer cover. The outer cover may be formed from a nonwoven web laminated to a thin plastic film. The film may be either liquid permeable or liquid impermeable and may be manufactured from, for example, polyethylene or polyolefin. The back ear portions may be extendible. Together, the back ear portions and the outer cover are configured to refasten ably secure the disposable absorbent article about a wearer. The discrete fastener elements embedded in the outer cover may be configured to increase the shear resistance and coefficient of friction between the outer cover and the back ear portions. The increased coefficient of friction and increased shear resistance may reduce relative surface-to-surface and radial movement of the front waist region relative to the back waist region and help to maintain the initial fastened position of the absorbent article.

The discrete fastener elements may be geometrically dispersed throughout the outer cover or may be concentrated in different areas of the outer cover to improve performance or fit. The absorbent article may also include additional discrete fastener element groups embedded in the outer cover in the front ear regions, embedded in the liner in the back ear portions, embedded in the flexible material of the mechanical fasteners, or combinations thereof. Each additional discrete fastener element group includes at least one discrete fastener element.

The discrete fastener elements embedded in the outer cover may have a lower profile height than the profile height of the outer cover and may have circular, rectangular, oval, or irregular cross sectional shapes. The discrete fastener elements may also be in the shape of lines. In various aspects, the discrete fastener elements may have the same cross sectional shapes within a particular discrete fastener element group or may include various cross sectional shapes within the same discrete fastener element group. The discrete fastener elements may have the same cross-sectional shapes from group to group or one or more discrete fastener element groups may include discrete fastener elements with different cross-sectional shapes. The discrete fastener elements may also have one or more protrusions extending from a garment-facing surface of the discrete fastener elements to increase shear resistance and coefficient of friction. The protrusions may be flexible or rigid. In various aspects the protrusions may be shaped in the forms of fingers, fins, nail heads, cones, blobs, mushrooms, fishhooks, or palm trees. All the discrete fastener elements of a discrete fastener element group may have protrusions or only some may have protrusions. The discrete fastener elements of a discrete fastener element group may have all the same shaped protrusions or may have more than one shaped protrusion with the same discrete fastener elements group. The protrusion shape of the discrete fastener elements of one discrete fastener element group may be different than the protrusion shape of the discrete fastener elements of a different discrete fastener element group. The protrusions may be configured to increase the shear resistance of the outer cover, the liner, the flexible layer or combinations thereof in the overlap region between the mechanical fastener and the ear portions and the front waist region of the absorbent article. Some or all of the protrusions throughout the absorbent article may be flexible or rigid.

For example, the outer cover of the absorbent article may include multiple discrete fastener element groups. Within one element group on the outer cover, there may be a mixture of discrete fastener elements, some elements having a circular cross-sectional shape and some elements having an oval cross-sectional shape. Another element group on the outer cover may include linear discrete fastener elements. Likewise, the liner material of the back ear portions may include one or more discrete fastener element groups. As with the outer cover, each discrete fastener element group on the liner material may have a mixture of discrete fastener elements of different cross-sectional shapes. Further, there may be differences in the cross-sectional shapes of the discrete fastener elements between the discrete fastener element groups. Each of the fastener element groups on the outer cover and the liner material may have discrete fastening elements having protrusions of various shapes.

Another aspect of the present invention relates to a disposable absorbent article. The disposable absorbent article may include an absorbent core located between an outer cover and a bodyside liner. The absorbent article may include a front waist region, a back waist region and a crotch region connecting the front and back waist regions. The front waist region may include front ear regions and the back waist region may include back ear portions. The back ear portions may further include a mechanical fastener. The back ear portions may further include a discrete fastener element group embedded therein. The discrete fastener element group may include at least one discrete fastener element.

The mechanical fastener may be located on the outer cover or the body side liner and may be positioned to bring the back waist region in communication with the front waist region when the absorbent article is applied. The mechanical fastener may be configured to refasten ably engage the front waist region. The discrete fastener element embedded in the back ear portions may be configured to increase the shear resistance and coefficient of friction between the back ear portions, the front ear regions and the front panel in the overlap region. The increased coefficient of friction and increased shear resistance may reduce relative surface-to-surface and radial movement of the front waist region relative to the back waist region and help maintain the initial fastened position of the absorbent article.

Together, the mechanical fastener and the front waist region are configured to refasten ably secure the disposable absorbent article about a wearer. The mechanical fastener may include hook material. The front and back ear portions may be extendible. The back ear portions may include a fastening material and may include a flexible layer. The fastening material may include a hook material that is refasten ably engageable with the front waist region.

The discrete fastener elements may be geometrically dispersed throughout the back ear portions or may be concentrated in different areas to improve performance or fit. The absorbent article may also include additional discrete fastener element groups embedded in the liner in the back ear portions and embedded in the flexible material of the mechanical fasteners, or combinations thereof. Each additional discrete fastener element group includes at least one discrete fastener element. In other aspects, the discrete fastener elements may have circular, rectangular, oval, or irregular cross-sectional shapes. The discrete fastener elements may also be in the shape of lines. The discrete fastener elements may have the same cross-sectional shapes within a particular discrete fastener element group or may include various cross-sectional shapes within the same discrete fastener element group. The discrete fastener elements may have the same cross-sectional shapes from group to group or one or more discrete fastener element groups may include discrete fastener elements with different cross-sectional shapes. The discrete fastener elements may also have one or more protrusions extending from a garment-facing surface of the discrete fastener elements to increase shear resistance and coefficient of friction. The protrusions may be shaped in the form of fingers, fins, nail heads, cones, blobs, mushrooms, fishhooks, or palm trees.

All the discrete fastener elements of a discrete fastener element group may have protrusions or only some may have protrusions. The discrete fastener elements of a discrete fastener element group may have all the same shaped protrusions or may have more than one shaped protrusion within the same discrete fastener elements group. The protrusion shape of the discrete fastener elements of one discrete fastener element group may be different than the protrusion shape of the discrete fastener elements of a different discrete fastener element group. The protrusions may be configured to increase the shear resistance of the liner or the flexible layer or both. Some or all of the protrusions throughout the absorbent article may be flexible or rigid. The discrete fastener elements act to increase the coefficient of friction between the back waist region and the front waist region when the back waist region is overlapped with the front waist region during use. The coefficient of friction reduces the radial shifting and shear slippage of the fastening system during use and improves the fit and performance of the absorbent article during use.

It is to be understood that both the foregoing general description and the following detailed description are exemplary and are intended to provide further explanation of the invention claimed. The accompanying drawings, that are incorporated in and constitute part of this specification, are included to illustrate and provide a further understanding of the articles and methods of the invention. Together with the description, the drawings serve to explain various aspects of the invention.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

FIG. 2 representatively shows a plan view of the landing zone of the absorbent article of FIG. 1;

FIG. 3 representatively shows a cross sectional view along line A-A of the landing zone of FIG. 2;

FIG. 11 representatively shows a magnified side elevation view of a sample protrusion shape in one aspect of the present invention;

FIG. 12 representatively shows a magnified side elevation view of a sample protrusion shape in one aspect of the present invention;

FIG. 13 representatively shows a magnified side elevation view of a sample protrusion shape in one aspect of the present invention;

FIG. 14 representatively shows a magnified side elevation view of a sample protrusion shape in one aspect of the present invention;

FIG. 15 representatively shows a magnified side elevation view of a sample protrusion shape in one aspect of the present invention;

DETAILED DESCRIPTION OF THE INVENTION

The present invention is directed to solving the problems related to the fit and performance of garments having mechanical fastening systems, particularly garments worn as absorbent articles. For example, the present invention is directed to solving the problem of radial shifting in the fastener overlap region in the front waist region of the absorbent article. It is important to control the position of the front waist region of the absorbent article because, in general, the front region of an absorbent article is more irregularly shaped than the back portion. Also, there is greater movement in the front waist portion due to the proximity of the wearer's abdomen and natural bending and flexing. The back waist portion in contrast tends to settle into the wearer's "small of the back." Radial shifting can cause a reduction in waist tension and leg tension that ultimately can cause a deterioration of fit and containment. Moreover, the present invention is directed to increasing the coefficient of friction and increasing the shear resistance in the fastener overlap region so that, in part, the mechanical fastening system is more secure and less likely to slip or shift during use. Further, the present invention is directed to solving the problem of decreased tension in the waist by maintaining the relative position of the fasteners during use.

The present invention encompasses mechanical fastening systems, particularly for use on disposable absorbent articles. When in use with disposable absorbent articles, the mechanical fastening systems of the present invention may be configured to secure the disposable absorbent article about the waist and legs of a wearer. Accordingly, the absorbent articles employing the mechanical fastening systems of the present invention may be configured to closely conform to the body of the wearer to effectively contain body exudates. In addition, the mechanical fastening systems of the present invention may be refastenable so that the absorbent article may be secured to and removed directly from the waist of the wearer and easily inspected to determine if the article has been soiled during use. As used herein, the term "disposable" refers to articles that are intended to be discarded after a limited use and which are not intended to be laundered or otherwise restored for reuse.

The mechanical fastening systems of the present invention will be described in terms of being used in combination with a disposable diaper article that is adapted to be worn by infants about the lower torso. It is understood that the mechanical fastening systems of the present invention are equally adaptable for other types of absorbent articles such as adult incontinent products, training pants, feminine hygiene products, other personal care or health care garments, diaper pants and similar types of articles.

Figure 1:
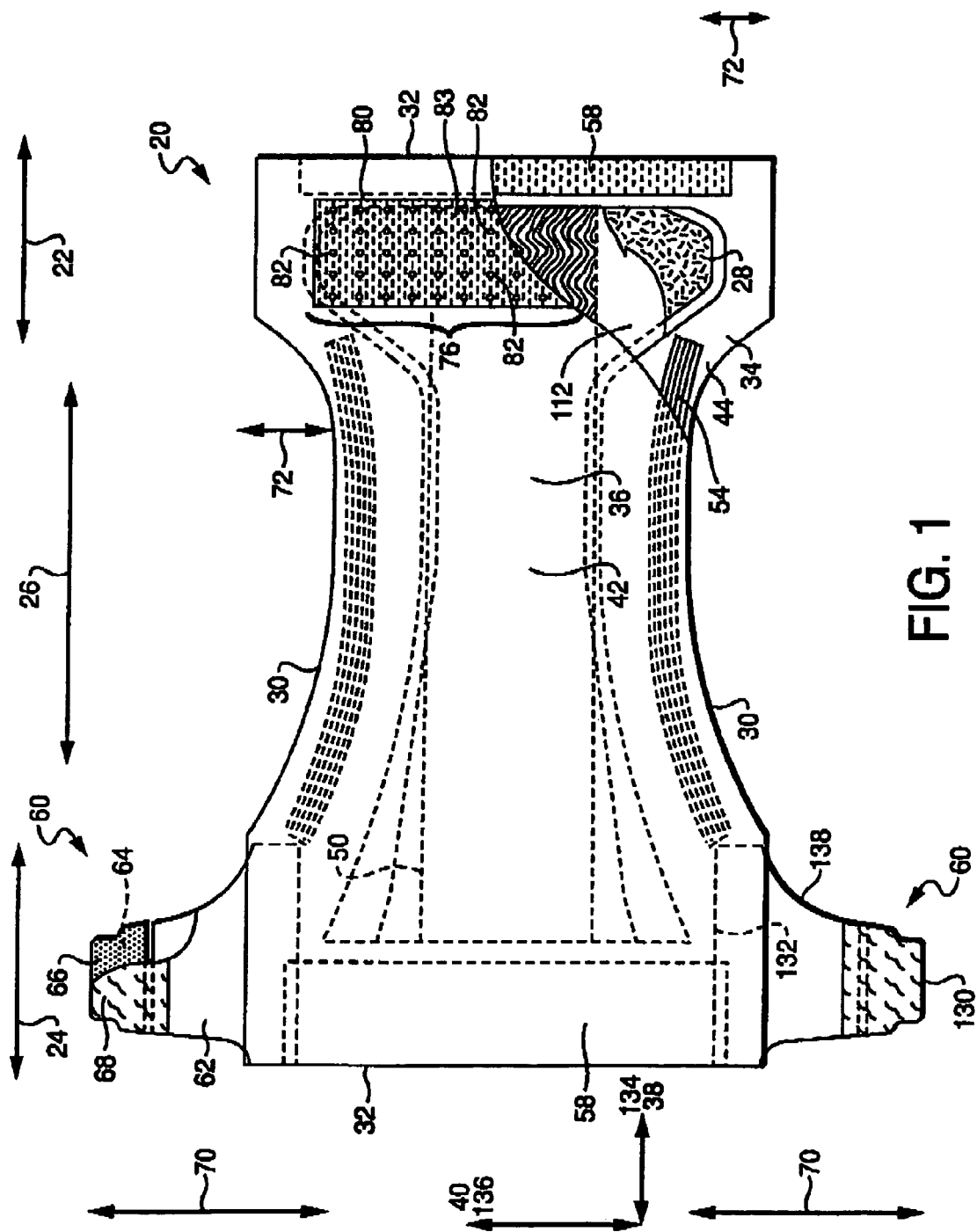
FIG. 1 representatively shows a plan view of one embodiment of an absorbent article in an unfastened, stretched and laid flat condition with the surface of the article which contacts the wearer's clothing facing the viewer and with portions of the article partially cut away to show the underlying features.

FIG. 1 representatively illustrates a mechanical fastening system of the present invention included in combination with a disposable diaper 20. In particular, the diaper 20 is shown in an unfastened, stretched and laid flat configuration with the surface of the diaper 20 adapted to contact the wearer's clothing facing the viewer and with portions of the diaper 20 partially cut away to show the underlying features. The illustrated diaper 20 defines a front waist region 22, a back waist region 24, a crotch region 26 that extends between and connects the front and back waist regions 22 and 24, a longitudinal direction 38 and a lateral direction 40. As used herein, the term "longitudinal direction" means the direction that is parallel to the machine direction of the diaper 20 and generally corresponds to the "y" direction of the diaper 20. As used herein the term "lateral direction" means the direction that is perpendicular to the machine direction of the diaper 20 and generally corresponds to the "x" direction of the diaper 20. The front waist region 22 includes the portion of the diaper 20 which, when worn, is positioned on the front of the wearer. The front waist region 22 further defines front ear regions 72 generally in the laterally outward portions of the front waist region 22. The back waist region 24 comprises the portion of the diaper 20 which, when worn, is positioned on the back of the wearer. The back waist region 24 further includes back ear portions 70. When the diaper 20 is worn, back ear portions 70 are overlapped with front ear regions 72. The crotch region 26 of the diaper 20 includes the portion of the diaper 20 which, when worn, is positioned between the legs of the wearer and covers the lower torso of the wearer.

Figure 16:
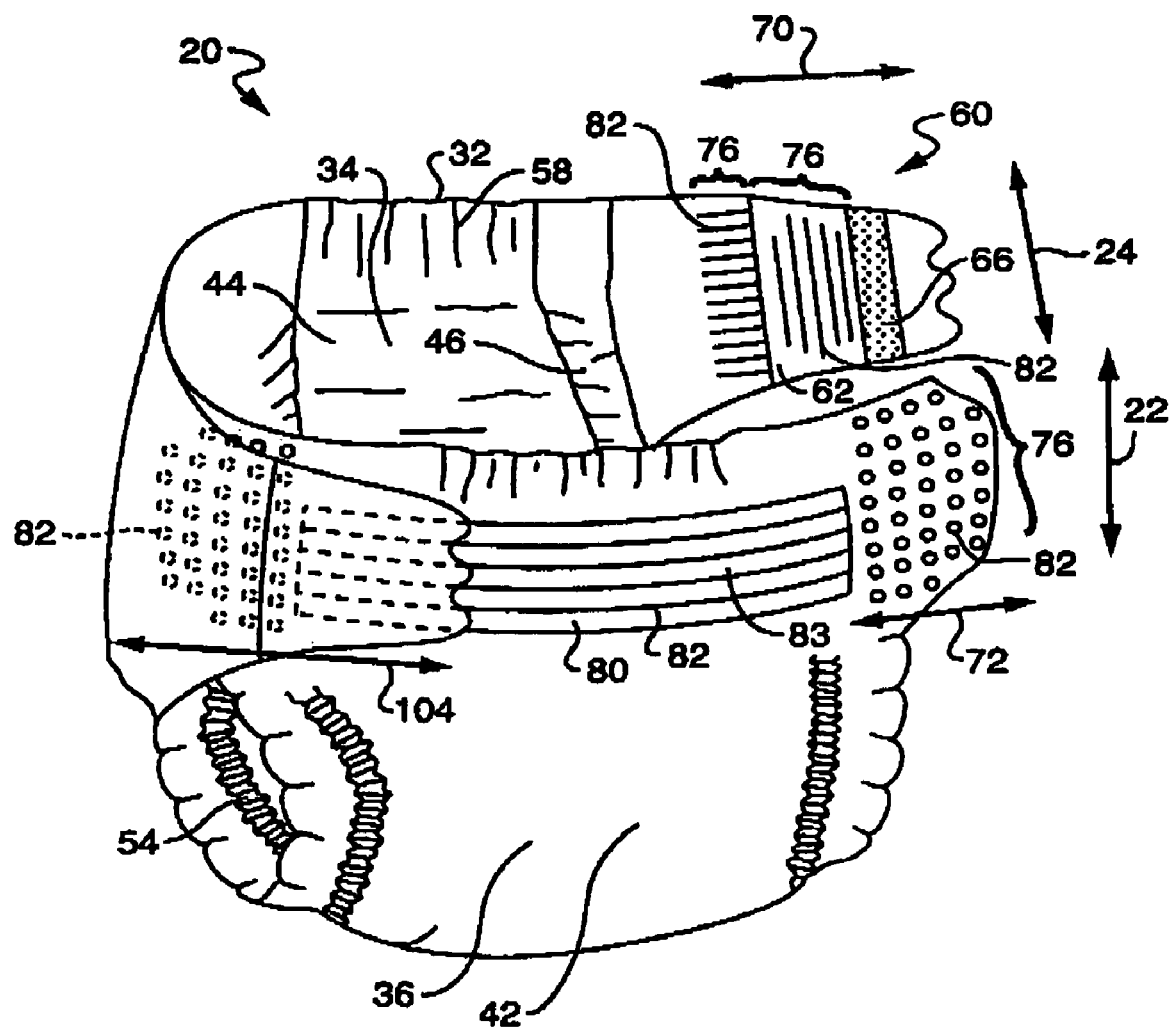
FIG. 16 representatively shows a front view of a partially fastened absorbent article showing two discrete fastener elements groups in back ear portions and two discrete fastener elements in the front waist region.

The diaper 20 defines a pair of laterally opposed side edges 30, a pair of longitudinally opposed waist edges 32, an interior surface 34 (facing away from the viewer) which is configured to contact the wearer, and an exterior surface 36, opposite the interior surface 34, which is configured to contact the wearer's clothing in use. The illustrated diaper 20 also includes an outer cover 42 and a bodyside liner 44 which is connected to the outer cover 42 in a superposed relationship and an absorbent core 28. The absorbent core 28 is located between the outer cover 42 and the bodyside liner 44. The laterally opposed side edges 30 of the diaper 20 are generally defined by the side edges 30 of the outer cover 42 which further define leg openings that are formed when the article is worn and may be curvilinear. The waist edges 32 of the diaper 20 are generally defined by the waist edges 32 of the outer cover 42 and define a waist opening which is configured to encircle the waist of the wearer when worn. The absorbent core 28 is configured to contain and/or absorb any body exudates discharged from the wearer. The diaper 20 may further include leg elastics 54, containment flaps 46 (as illustrated in FIG. 16) and waist elastics 58 as are known to those skilled in the art. It should be recognized that individual components of the diaper 20 may be optional depending upon the intended use of the diaper 20.

As illustrated in FIG. 1, the diaper 20 may include a back ear portion 70 attached in the back waist region 24. The back ear portion 70 may include fasteners 60 and part of the outer cover 42 and the liner 44. The fastener 60 may comprise a flexible layer 62, a mechanical fastening material 66, and a backing material 68 attached to the mechanical fastening material 66. The mechanical fastening material 66 defines a fastening surface 64 opposite the backing material 68. The mechanical fastener 60 may also define a user's end 130, a manufacturer's bond end 132, a fastener longitudinal direction 134, and a fastener lateral direction 136. As used herein, the term "fastener longitudinal direction" means the direction that is parallel to the centerline of an absorbent article when a fastener 60 is attached to an absorbent article and generally corresponds to the "y" direction of the fastener 60. As used herein, the term "fastener lateral direction" means the direction that is perpendicular to the centerline of an absorbent article when a fastener 60 is attached to an absorbent article and generally corresponds to the "x" direction of the fastener 60.

Figure 4:
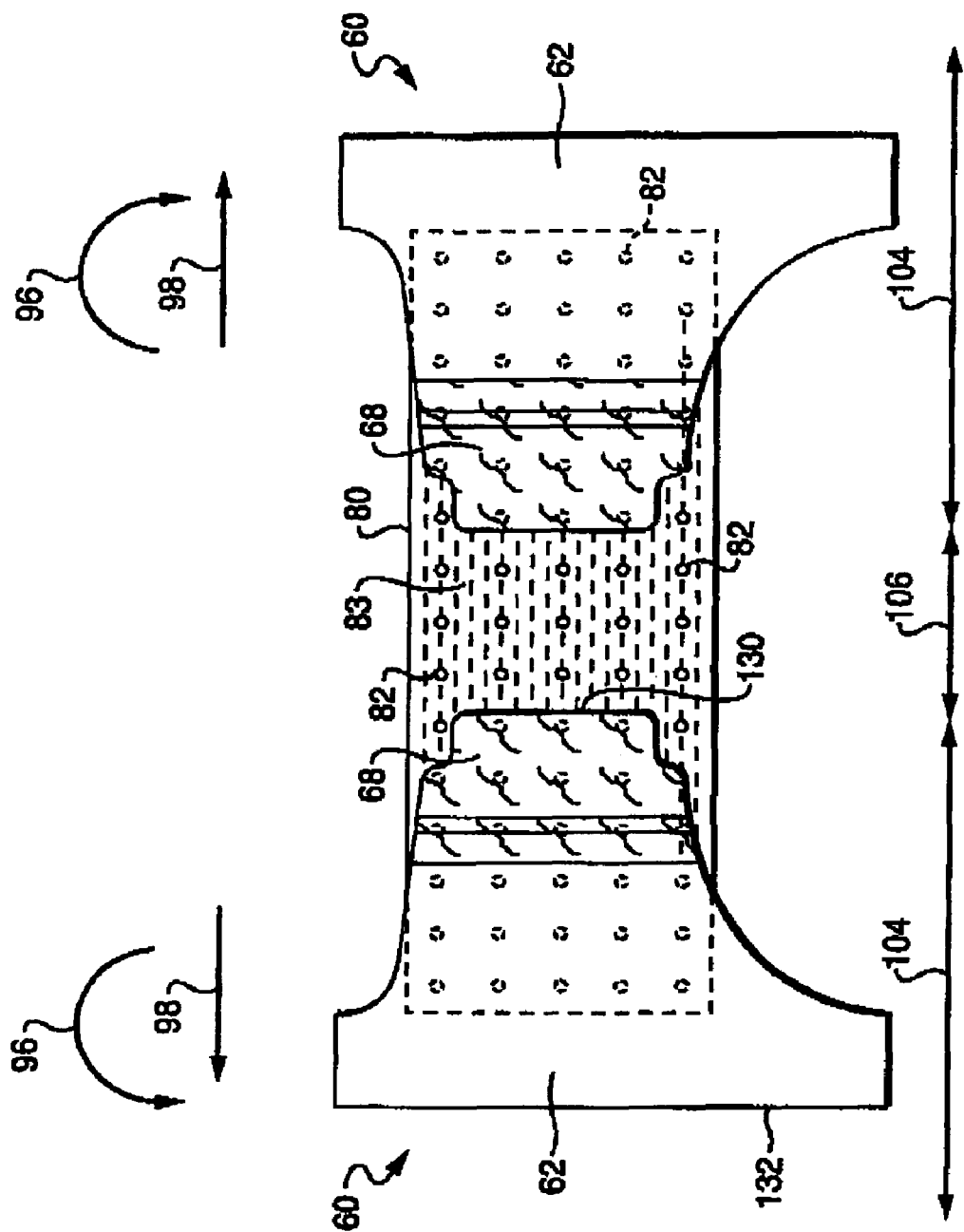
FIG. 4 representatively shows a simplified view of the fastening system of FIG. 1 in a fastened configuration in order to illustrate the relationship between the landing zone, the ear portions and the mechanical fasteners.

FIG. 1 representatively illustrates an example of the mechanical fastening system of the present invention. The mechanical fastening system includes mechanical fasteners, as generally indicated at 60, a landing zone 80, and a discrete fastener elements group 76 including a plurality of discrete fastener elements 82. The landing zone 80 may be associated with the outer cover 42 in the front waist region 22 of the diaper 20 between the front ear regions 72. The landing zone 80 includes a base material 83 and a discrete fastener elements group 76 which is embedded in the base material 83. The mechanical fasteners 60 may include a fastening material 66. In use, the wearer overlaps the back ear portion 70 over the front waist region 22 and engages the fastening material 66 of the fastener 60 to the base material 83 of the landing zone 80, as illustrated in FIGS. 4 and 16, creating the overlap region 104. The discrete fastener elements 82 contact the mechanical fasteners 60, in the overlap region 104, and increase the shear resistance between the landing zone 80 and the mechanical fasteners 60 and decrease the overall radial shifting between the landing zone 80 and the mechanical fasteners 60. The decrease in radial shifting helps maintain the position of the back waist region 24 of the diaper 20 relative to the position of the front waist region 22 of the diaper 20 improving overall fit and performance.

This aspect of the present invention may further include additional discrete fastener elements groups 76 in the front ear regions 72, back ear portions 70, or both. The additional discrete fastener elements groups 76 in the back ear portions 70 may be embedded in the liner material 44, the flexible layer 62, or both. The additional discrete fastener elements groups 76 may include at least one discrete fastener elements 82 or may include a plurality of discrete fastener elements 82. The additional discrete fastener elements groups 76 in the front ear regions 72 are configured to contact the back ear portions 70 when the back ear portions 70 are overlapped with the front waist region 22 during use. The discrete fastener elements 82 in the additional discrete fastener elements groups 76 in the front ear regions 72 may specifically contact the liner 44, the flexible layer 62, or both to increase the coefficient of friction and reduce radial shifting and shear slippage. The discrete fastener elements 82 in the back ear portion 70 are configured to contact the landing zone 80, the outer cover 42 in the front ear regions 72, or both when the back ear portions 70 are overlapped with the front waist region 22 during use. These points of contact may increase the coefficient of friction and reduce radial shifting and shear slippage between the back ear portions 70 and the front waist region 22.

FIG. 16 illustrates a diaper 20 in a partially fastened configuration. The diaper 20 includes a landing zone 80 in the front waist region 22. The landing zone 80 includes a discrete fastener elements group 76 embedded in the base material 83. The discrete fastener elements group 76 includes a plurality of discrete fastener elements 82 that are linear in cross-sectional shape. The diaper 20 further includes a discrete fastener elements group 76 in both front ear regions 72. The discrete fastener elements groups 76 in the front ear regions 72 include a plurality of discrete fastener elements 82 with generally circular cross-sectional areas. The back waist region 24 of diaper 20 includes mechanical fasteners 60. The mechanical fasteners 60 include a flexible layer 62 and a fastening material 66. The flexible layer 62 includes a discrete fastener elements group 76 embedded therein. The discrete fastener elements group 76 embedded in the flexible layer 62 includes a plurality of discrete fastener elements 82 that are generally linear in cross-sectional area. The diaper 20 further includes a discrete fastener elements group 76 embedded in the liner 44 in the back ear portion 70. The discrete fastener elements group 76 includes a plurality of discrete fastener elements 82 that are generally linear in cross-sectional area. Combined, the discrete fastener elements groups 76 are configured to increase the coefficient of friction and reduce shear slippage in the overlap region 104 thus improving fit and performance. Specifically, the fastening material 66 is configured to engage the base material 83 of the landing zone 80. The discrete fastener elements group 76 embedded in the flexible layer 62 is configured to contact the outer cover 42 in the front ear region 72, the base material 83, or both. The discrete fastener elements group 76 embedded in the liner 44 in the back ear portion 70 is configured to contact the outer cover 42 in the front ear region 72, the base material 83, or both. The discrete fastener elements group 76 embedded in the outer cover 42 in the front ear regions 72 are configured to contact the flexible material 62 of the mechanical fastener 60, the liner 44, or both. The discrete fastener elements group 76 embedded in the base material 83 of the landing zone 80 is configured to contact the flexible layer 62 of the mechanical fastener 60, the liner 44, or both. In use, these points of contact increase the coefficient of friction between the back waist region 24 and the front waist region 22 in the overlap regions 104 decreasing radial shifting and shear slippage.

The various discrete fastener element groups and discrete fastener elements representatively illustrated in FIG. 16 can be formed by applying the desired polymer material to the various nonwoven components. For example, the selected polymer may be printed in the desired shape on to the nonwoven component. For example, the discrete fastener elements group 76 embedded in the base material 83 of the landing zone 80 may be printed onto the base material 83 either before the landing zone is applied to the diaper 20 (if the landing zone 80 is a separate component) or during manufacture of the diaper 20. In addition to printing, the discrete fastener elements may be extruded onto the various base materials using techniques that are known in the art for forming conventional mechanical fastening materials.

FIG. 2 representatively illustrates the landing zone 80 of FIG. 1 including a discrete fastener elements group 76. The discrete fastener elements group 76 includes a plurality of discrete fastener elements 82 embedded in the base material 83. FIG. 3 representatively illustrates a cross-sectional view of the landing zone 80 of FIG. 2 along line A-A.

Figure 8:
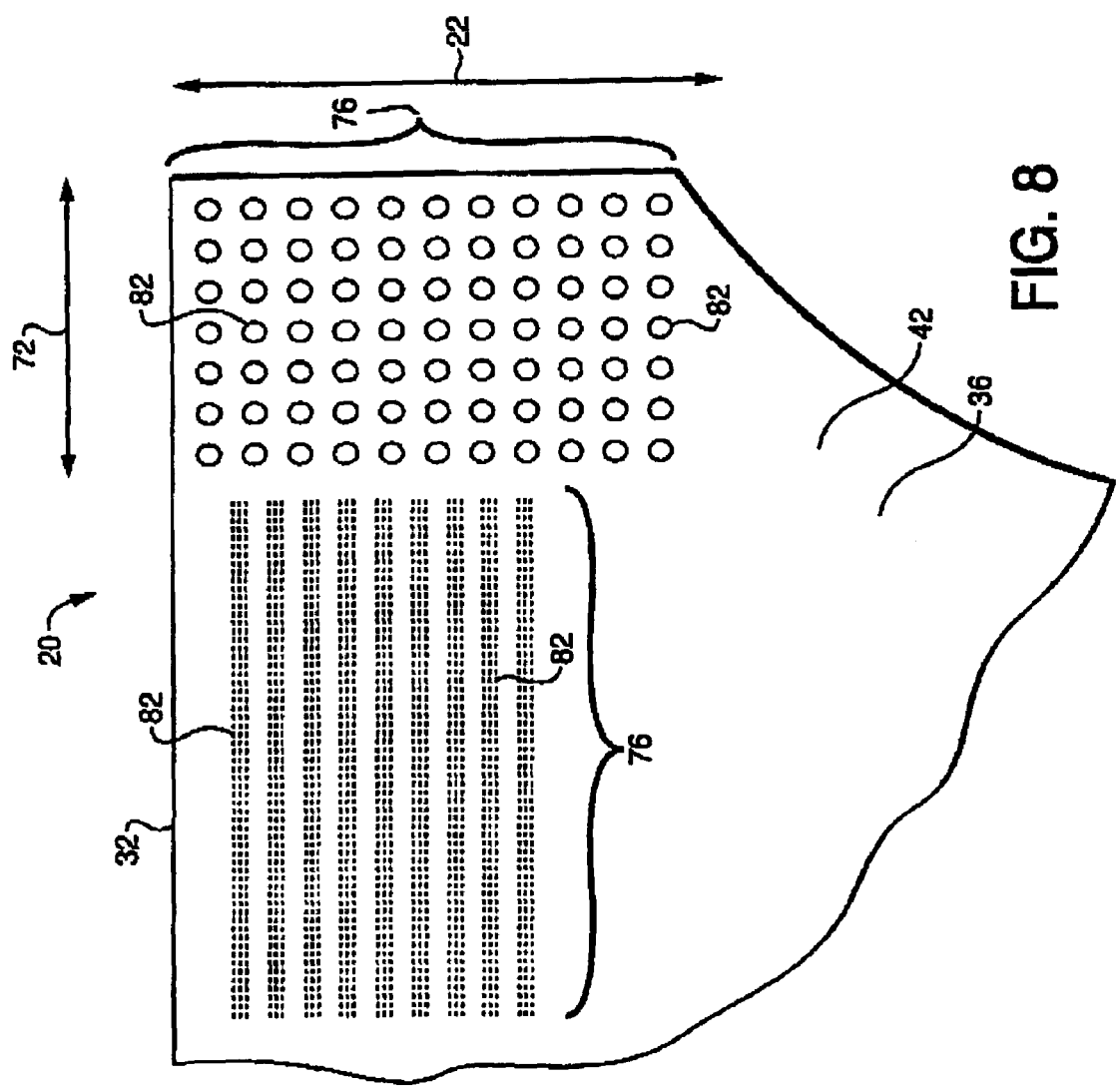
FIG. 8 representatively shows a plan view of another aspect of the improved fastening system of the present invention in an unfastened laid flat view, with the outer cover surface facing the view, showing two different discrete fastener elements groups in the front waist region.
Figure 10:
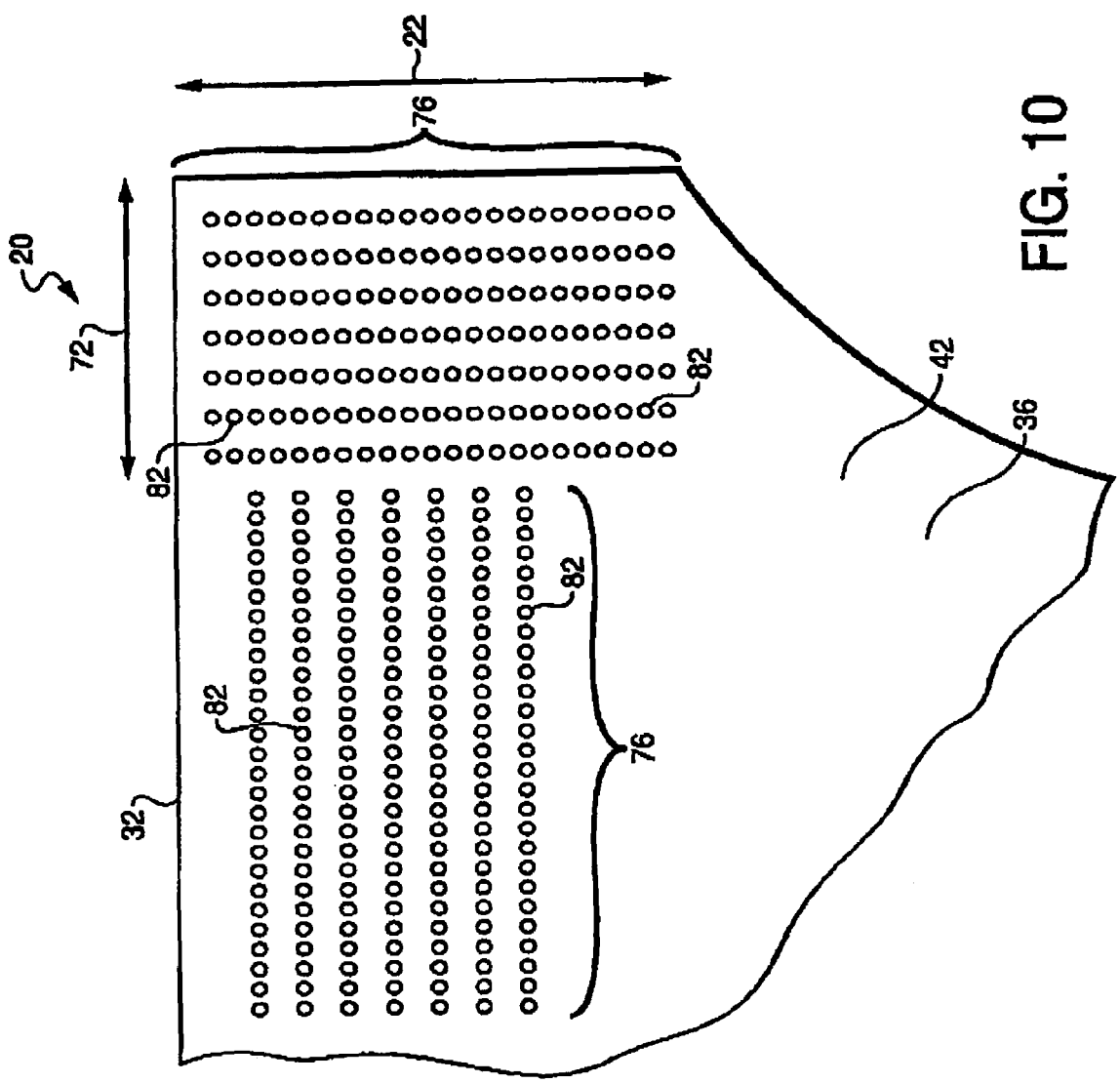
FIG. 10 representatively shows a plan view of another aspect of the improved fastening system of the present invention in an unfastened laid flat view, with the outer cover surface facing the view, showing two different discrete fastener elements groups in the front waist region.

In another aspect of the present invention a discrete fastener elements group 76 may be embedded directly in the outer cover 42 in the front waist region 22 of the diaper 20 as illustrated in FIGS. 8 and 10. The discrete fastener elements group 76 includes a plurality of discrete fastener elements 82. The fastening material 66 of the mechanical fastener 60 may engage the outer cover 42 directly. The discrete fastener elements 82 of discrete fastener elements group 76 may be embedded in the outer cover 42 in the front waist region 22 of the diaper 20 and may contact the flexible layer 62 of the mechanical fastener 60, the liner 44 in the back ear portion 70, or both. The points of contact with the discrete fastener elements 82 increases the shear resistance between the outer cover 42 and the back waist region 24 and decreases the radial shifting between the front waist region 22 and the back waist region 24 in the overlap region 104.

Figure 7:
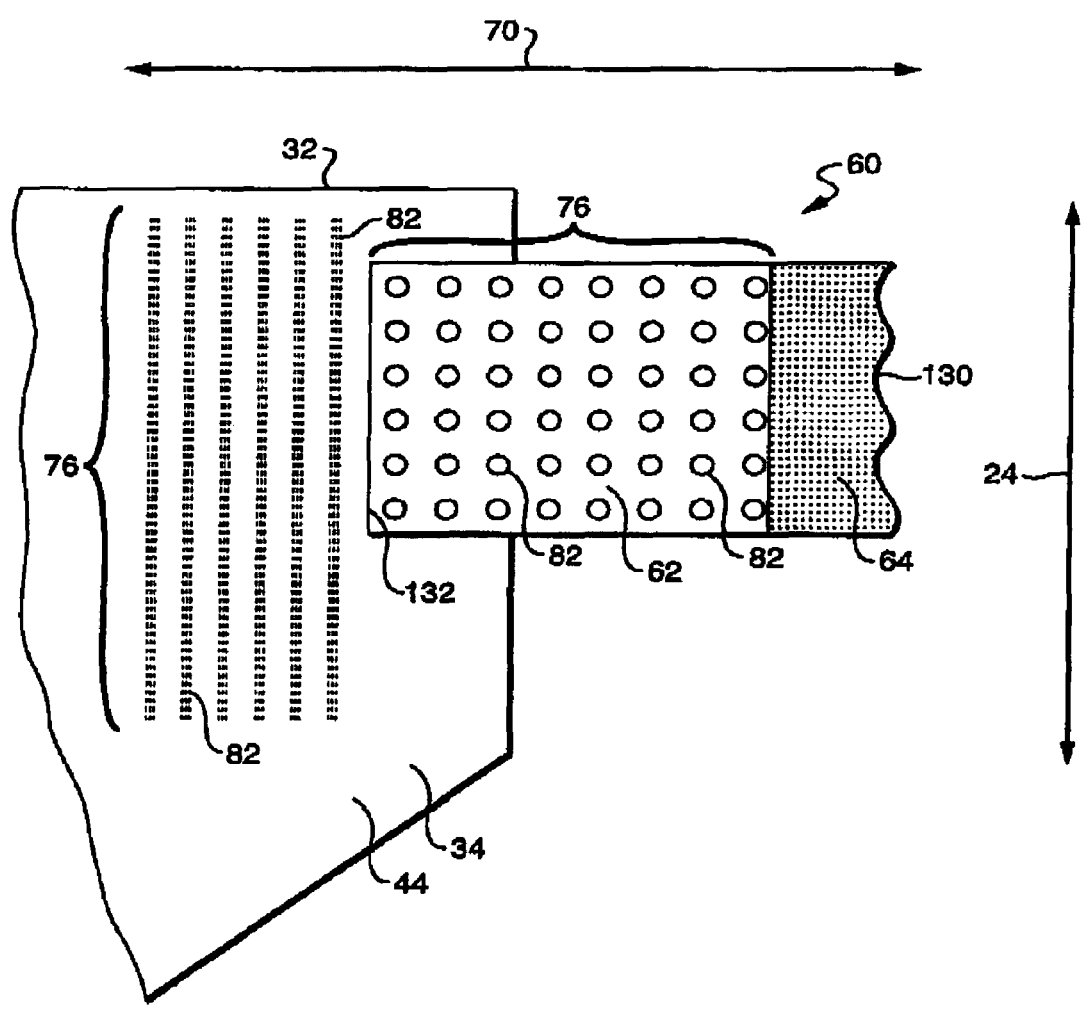
FIG. 7 representatively shows a plan view of another aspect of the improved fastening system of the present invention in an unfastened laid flat view, with the liner surface facing the viewer; showing two different discrete fastener elements groups in the back ear portion.
Figure 9:
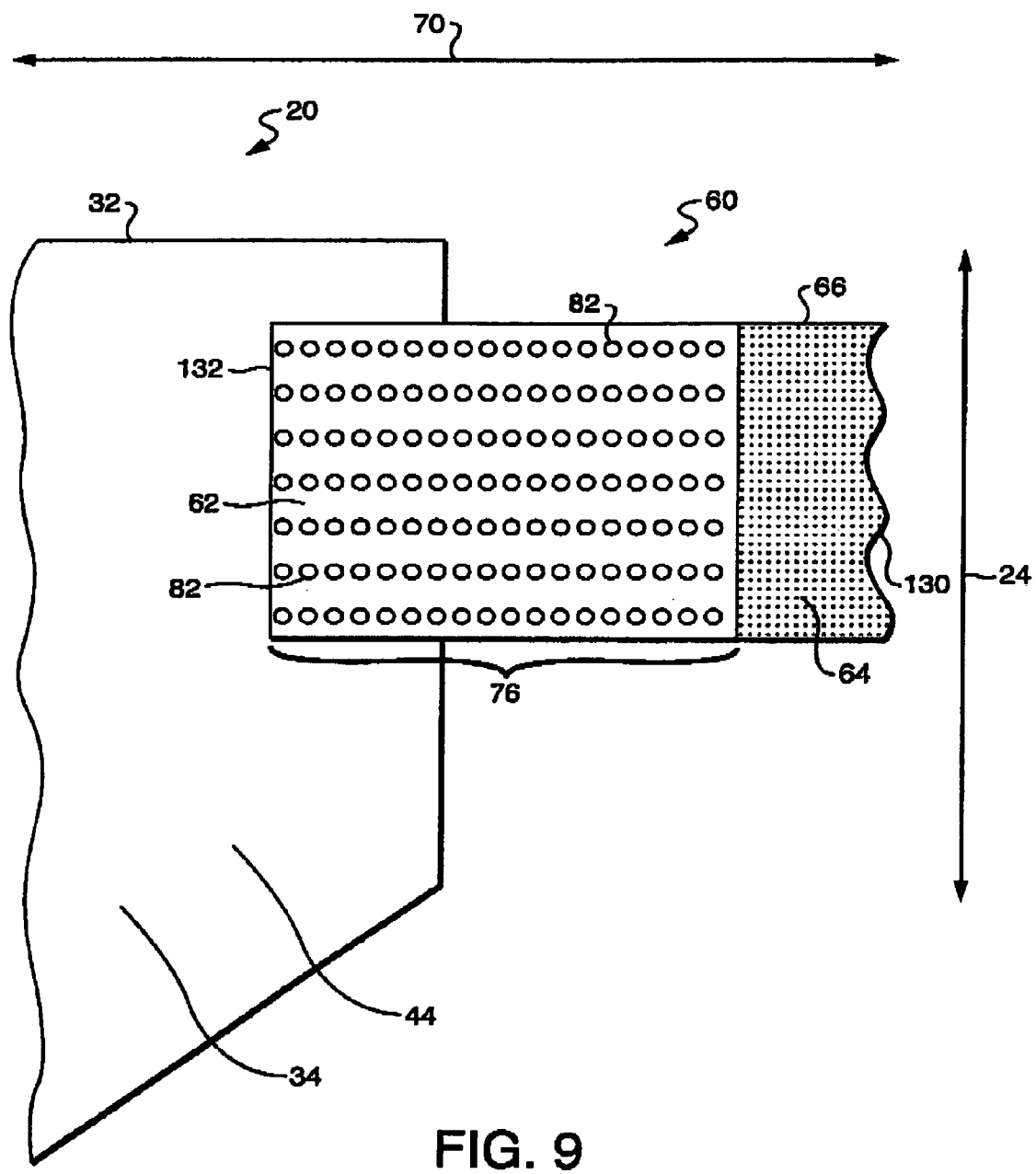
FIG. 9 representatively shows a plan view of another aspect of the improved fastening system of the present invention in an unfastened laid flat view, with the liner surface facing the viewer, showing a discrete fastener elements group.

Referring to FIGS. 7-10, this aspect of the present invention may further include additional discrete fastener elements groups 76 in the front ear regions 72, back ear portions 70, or both. The additional discrete fastener elements groups 76 in the back ear portions 70 may be embedded in the liner material 44, the flexible layer 62 as illustrated in FIG. 9, or both as illustrated in FIG. 7. The additional discrete fastener elements groups 76 may include at least one discrete fastener elements 82 or a plurality of discrete fastener elements 82 as illustrated in FIGS. 7-10. The additional discrete fastener elements groups 76 in the front ear regions 72 are configured to contact the back ear portions 70 when the back ear portions 70 are overlapped with the front waist region 22 during use. The discrete fastener elements 82 in the additional discrete fastener elements groups 76 in the front ear regions 72 may specifically contact the liner 44, the flexible layer 62, or both to increase the coefficient of friction and reduce radial shifting and shear slippage. The discrete fastener elements 82 in the back ear portion 70 are configured to contact the outer cover 42 and the front ear regions 72 when the back ear portions 70 are overlapped with the front waist region 22 during use. These points of contact may increase the coefficient of friction and reduce radial shifting and shear slippage between the back ear portions 70 and the front waist region 22.

FIG. 8 representatively illustrates an aspect of the present invention whereby the front waist region 22 includes two discrete fastener elements groups 76 and whereby the discrete fastener elements groups 76 include discrete fastener elements 82 with different cross-sectional shapes. The discrete fastener elements groups 76 include a plurality of discrete fastener elements 82. One discrete fastener elements group 76 includes linear discrete fastener elements 82 in the front waist region 22 of diaper 20. The second discrete fastener elements group 76 includes discrete fastener elements 82 with a circular cross sectional shape in the front ear region 72 of the front waist region 22. FIG. 10 alternatively illustrates another aspect of the present invention whereby the first discrete fastener elements group 76 and the second discrete fastener elements group 76 include discrete fastener elements 82 that have a circular cross sectional shape.

In yet another aspect of the present invention, the discrete fastener elements groups 76 may only be included in the back ear portions 70. The discrete fastener elements group 76 of this aspect may be embedded directly in the liner material 44, the flexible layer 62 of the mechanical fastener 60 as illustrated in FIG. 9, or both as illustrated in FIG. 7.

The discrete fastener elements 82 may include at least one discrete fastener element 82 or a plurality of discrete fastener elements 82. FIG. 7 representatively illustrates the use of a discrete fastener elements group 76 including discrete fastener elements 82 embedded in the liner 44 in the back ear portion 72 in the back waist region 24 of the diaper 20. FIG. 7 represents an aspect of the present invention wherein the first discrete fastener elements group 76 includes discrete fastener elements 82 with a linear cross-sectional shape embedded on the liner 44. FIG. 7 further illustrates a second discrete fastener elements group 76 including discrete fastener elements 82 with a circular cross sectional shape embedded on the flexible layer 62 of mechanical fastener 60. The back waist region 24 is stabilized in the overlap region 104 when overlapped with the front region 22 upon donning and during use. The back region 24 is stabilized relative to the front region 22, in part, because of the increased coefficient of friction in the overlap region 104 resulting from the discrete fastener elements 82.

FIG. 9 representatively illustrates an alternative pattern of discrete fastener elements 82 in the back waist region 24 of diaper 20. In this aspect, the discrete fastener elements group 76 including the discrete fastener elements 82 are embedded in the flexible layer 62 of the mechanical fastener 60. The discrete fastener elements 82 are circular in cross-section and linear in pattern.

Figure 5:
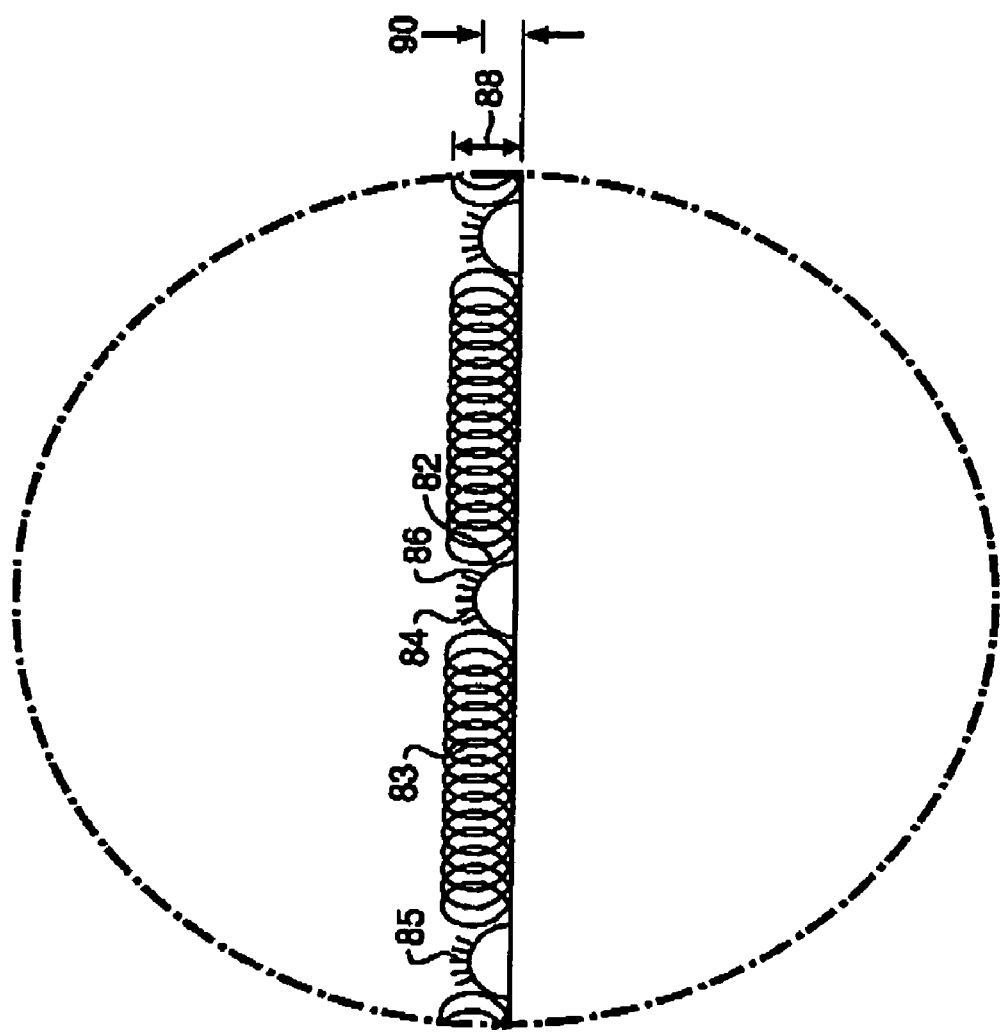
FIG. 5 representatively shows a magnified view of a portion of the fastener landing zone of FIG. 3.

In various aspects of the present invention, the discrete fastener elements 82 may be configured to be "skin friendly." "Skin friendly" as used herein refers to an absorbent article that is pleasant to the touch and does not cause red marking or irritation of the user's skin. FIG. 5 is a magnified view of a portion of the landing zone 80 of FIG. 3 and representatively illustrates the relative height of the discrete fastener element profile height 90 of the discrete fastener element 82 and the profile height 88 of the surrounding material 88. In various aspects, the surrounding material may be base material 83 of the landing zone 80, outer cover 42, liner 44, or flexible layer 62. The discrete fastener element profile height 90 may be lower than the surrounding material profile height 88. In certain aspects of the current invention, the lower fastener element profile height 90 allows the fastening material 66 of the mechanical fasteners 60 to more easily engage the base material 83 of the landing zone 80 without interference from the discrete fastener elements 82. The lower discrete fastener profile height 90 may also provide a more appealing feel to the landing zone 80 in the exposed region 106 and reduces the amount of undesired engagement with the landing zone 80, such as from clothing or lint. However, in the overlap region 104, the engagement of the fastening material 66 of the mechanical fastener 60 can compress the base material 83 thus allowing the discrete fastener elements 82 to contact the flexible layer 62 of the mechanical fasteners 60 and increase the coefficient of friction and shear resistance between the back waist region 24 and the front waist region 22 in the overlap region 104. In other aspects, the lower profile height 90 of the discrete fastener elements 82 may result in a more skin friendly outer cover 42, liner 44, or flexible layer 62 while still increasing the coefficient of friction and resistance to shear forces.

In various aspects of the present invention, the discrete fastener elements 82 of the discrete fastener elements groups 76 may be formed in a variety of cross-sectional shapes. As illustrated in FIGS. 2 and 5, the discrete fastener elements 82 can be semi-spherical with a circular cross-sectional shape. The discrete fastener elements 82 may also have rectangular, oval, or irregular cross-sectional shapes. Alternatively, the discrete fastener elements 82 may be generally linear and continuous as illustrated in FIGS. 7, 8, and 16. Discrete fastener elements 82 may all have the same cross-sectional shapes within the same discrete fastener elements group 76 or at least one discrete fastener element 82 may have a different cross sectional shape within the same discrete fastener element group 76. Discrete fastener elements 82 of different discrete fastener elements groups 76 may all have the same cross-sectional shapes or at least one discrete fastener element 82 may have a different cross sectional shape than a discrete fastener element 82 in a different discrete fastener element group 76.

In various aspects of the present invention, the discrete fastener elements 82 may be dispersed throughout the discrete fastener elements groups 76 in a variety of ways. For example, the discrete fastener elements 82 may be geometrically dispersed in the discrete fastener elements groups 76 in a circular, rectangular or triangular pattern. Alternatively, the discrete fastener elements 82 may be concentrated in the areas of the discrete fastener elements groups 76 onto which the user is most likely to engage a complementary mechanical fastener 60. In certain aspects, the discrete fastener elements 82 may have a higher concentration of coverage on the outboard sides of the fastener landing zone 80 to increase the area of the base material 83 of the landing zone 80 available for engagement by the fastening material 66 of the mechanical fastener 60. Also, the discrete fastener elements 82 can be randomly dispersed throughout the base material 83 of the landing zone 80. The discrete fastener elements groups 76 may have the same pattern of discrete fastener elements 82 or at least one discrete fastener elements group 76 may have a different discrete fastener elements 82 pattern.

In various aspects of the present invention, the discrete fastener elements 82 have a garment facing surface 86 and may have at least one protrusion 84 extending from the garment facing surface 86, as illustrated in FIG. 5. The protrusions 84 may have an upper surface 85 and may be formed in a variety of shapes. Referring to FIGS. 11-15 for example, the protrusions 84 may be shaped like fingers (FIG. 13), fins, mushrooms, nail heads (FIG. 11), cones (FIG. 12), fishhooks, blobs (FIG. 14) or palm trees. The protrusions 84 may be generally perpendicular to the garment facing surface 86 or the protrusions 84 may form an angle of less than 90° with the garment facing surface 86. The protrusions 84 may be rigid or flexible. The protrusions 84 may all have the same shape within the same discrete fastener elements group 76 or at least one protrusion 84 may have a different shape within the same discrete fastener elements group 76. The protrusions 84 may all have the same shape between different discrete fastener elements groups 76 or the protrusions 84 on the discrete fastener elements 82 of at least one discrete fastener elements group 76 may have a different shape than the protrusions 84 of another discrete fastener elements group 76.

The discrete fastener elements 82, as representatively illustrated in FIGS. 1-10 and 16, may suitably be formed of a thermoplastic polymer such as METALLOCENE polymer, PEBAX polymer, KRATON polymer, polyethylene, polypropylene, polyurethane, polystyrene, polycarbonate, polyester, ethylene vinyl acetate, ethylene vinyl alcohol, ethylene vinyl acetate acrylate, or ethylene acrylic acid copolymers. As previously described herein, the discrete fastener elements 82 may be formed from a selected thermoplastic polymer on the desired base material using techniques known to those of skill in the art such as printing or extrusion.

The landing zone 80 of the present invention works in cooperation with the mechanical fastener 60 to secure the disposable absorbent article about the wearer. The base material 83 of the landing zone 80 can be any material suitable for engagement with the mechanical fastener 60. The base material 83 may be provided by a variety of materials as are well known to those skilled in the art. Suitable materials can include woven or nonwoven loop materials. For example, the base material 83 can be a nonwoven fabric having continuous bonded areas defining a plurality of discrete unbonded areas. The unbonded areas can be specifically designed to afford spaces sufficiently open or large to receive and engage hook elements of a complimentary hook material. One suitable base material 83 is described in U.S. Pat. No. 5,858,515 issued Jan. 12, 1999, to Stokes et al., the disclosure of which is herein incorporated by reference in a manner that is consistent (not contradictory) herewith.

The mechanical fastener 60 of the present invention includes a flexible layer 62. The flexible layer 62 generally provides the chassis for the fastener 60. However, in some aspects of the present invention, the flexible layer 62 may provide the base for the discrete fastener elements 82 as representatively illustrated in FIGS. 7 and 9. The flexible layer 62 desirably provides a feeling of flexibility and softness to the wearer. The flexible layer 62 may be provided by a variety of materials as are well known to those skilled in the art. For example, the flexible layer 62 may be provided by knits, wovens, fabrics, papers, foams, reticulated films, nonwovens, and similar materials, or combinations thereof. Various types of nonwoven materials may be advantageously used as the flexible layer 62, such as a thermally or chemically bonded carded web or a nonwoven laminate. Examples of nonwoven laminates that may be advantageously used as the flexible layer 62 include stretchable neck bonded laminates, such as those disclosed in U.S. Pat. No. 5,789,065 issued on Aug. 4, 1998 to Haffner et al. and U.S. Pat. No. 5,336,545 issued on Aug. 9, 1994 to Morman. Alternatively, relatively inelastic nonwoven laminates, such as a spunbond/meltblown/spunbond composite may also be advantageously used. Desirably, the flexible layer 62 is provided by a nonwoven such as a neck bonded laminate or a thermally bonded carded web. In particular, it is desirable that the fibers of the flexible layer 62 be sufficiently fine such that the flexible layer 62 is accordingly soft to the touch.

The flexible layer 62 of the fastener 60 generally provides the shape of the fastener 60. That is, the perimeter edge 138 of the flexible layer 62 defines the profile or shape of the fastener 60. As such, the fastener 60 may have a variety of suitable shapes as are well known to those in the art. For example, as representatively illustrated in FIGS. 1 and 4, the fastener 60 may have a curvilinear shape that may improve the comfort of the wearer by better conforming to the contours of the wearer's body. Alternatively, the flexible layer 62 may provide the fastener 60 with a generally rectangular shape.

Desirably, the flexible layer 62 is extensible or elastic in at least the fastener lateral direction 136. For example, the flexible layer 62 may be comprised of a stretch-thermal laminate (STL) neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Morman, and European Patent No. EP 0 217 032 B1 issued on Feb. 19, 1992 to Taylor et al., the disclosures of which are hereby incorporated by reference.

The flexible layer 62 may include a single piece of material or multiple pieces of material. For example, the flexible layer 62 may include multiple pieces of material in the fastener lateral direction 136. As such, the flexible layer 62 may include an extensible panel located between a pair of generally non-extensible flexible materials to provide a flexible layer 62 that is extensible, as described above. Alternatively, the flexible layer 62 may include multiple pieces of material that are arranged in layers in the third direction 52.

The fastening material 66 allows the fastener 60 to refasten ably engage the landing zone 80 of the diaper 20, thereby securing the diaper 20 about the wearer in use. Suitable fasteners to provide the fastening material 66 are well known to those skilled in the art and can include, hook material, loop material, mushroom material, and similar fastening material, and combinations thereof. Desirably, in one aspect, the fastening material 66 is a hook type fastener material. As such, the fastening surface 64 may contain multiple hooks.

The term "hook" should be understood to encompass various geometries of protuberances that are suitable for engaging into a loop material or a material having loop characteristics in order to place or secure a fastener. Exemplary geometries include prongs, stems, trees (such as the shapes connoted by "evergreen" and "palm" trees), mushrooms, J-hooks, bidirectional hooks and studs protruding at various angles. In addition to the various possible geometries of hooks, the hooks may protrude from a backing material at various angles. U.S. Pat. No. 5,782,819 issued to Tanzer et al. on Jul. 21, 1998 describes a fastener system that includes velvet fabrics as examples of materials exhibiting differential friction. The surface of velvet fabric has fibers protruding from the surface, oriented on a bias. Despite the fibers being essentially straight (i.e. without barbs or hooks), they engage an opposed surface and facilitate fastening. The discrete hooks of the hook material may include or be treated with materials such as soft rubbers that increase the coefficient of friction of the hooks against the corresponding loop/engaging material. The increased coefficient of friction serves to reduce the tendency of the fastener to pop-open under stress. The benefits of fasteners having increased coefficients of friction are described in U.S. patent application Ser. No. 09/705,512 entitled "Hook and Loop Fastener Having an Increased Coefficient of Friction" filed by Martin et al. on Nov. 3, 2000.

Desirably, the fastening material 66 of the fastening surfaces 64 of this embodiment of the present invention is a hook fastener material, as already described in detail herein. In particular, the fastening material 66 may be VELCRO HTH 858 or VELCRO HTH 1303, or a similar hook material.

As representatively illustrated in FIG. 1, the mechanical fastener 60 of the present invention may further define a manufacturer's bond end 132 and a user's end 130. As used herein, reference to a manufacturer's bond end 132 is intended to refer to that portion of a fastener which is attached to the diaper 20 by the manufacturer of the diaper as part of the diaper production process. That is, the manufacturer's bond end 132 is generally intended to be permanently attached to the diaper 20. Likewise, as used herein, reference to a user's end 130 is intended to refer to that portion of the fastener 60 that is used by the wearer or care giver to secure the diaper 20 about the waist of the wearer, and which generally includes the fastening surfaces 64. The user's end 130 of the mechanical fastener 60 is generally designed to be refastenable such that the diaper 20 can be fastened and refastened about a wearer through the use of the user's end 130 of the mechanical fastener 60. Thus, the attachment formed by the user's end 130 of the mechanical fastener 60 is generally nonpermanent.

Methods of bonding the fastener 60 to the diaper 20 to define the bond end 132 are well known to those skilled in the art. For example the mechanical fasteners 60 may be permanently adhered to the side edges 30 of the diaper 20 by adhesive bonds, sonic bonds, thermal bonds, and the like, or combinations thereof. As discussed above, the method of attachment used to form the bond end 132 is generally intended to be permanent. Desirably, the bond end 132 is attached to the diaper 20 using ultrasonic bonding techniques for reduced manufacturing cost.

The discrete fastener elements 82 may be fused to the base material 83 by extruding intermittent quantities of molten polymer onto the base material 83. Alternatively, the discrete fastener elements 82 may be formed as continuous lines of polymer onto the base material 83. The protrusions 84 may be formed simultaneously with the discrete fastener elements 82. An example of a method of forming discrete fastener elements 82 suitable for use in connection with the instant application is described in PCT application WO 00/50229, published Aug. 31, 2000, to Tuman et al.

The diaper 20 may be of various suitable shapes. For example, in the unfastened configuration as illustrated in FIG. 1, the diaper 20 may have an overall rectangular shape, T-shape or a generally I-shape. In the shown embodiment, the diaper 20 has an approximately hourglass shape in an unfastened configuration. Examples of diaper configurations suitable for use in connection with the instant application and other diaper components suitable for use on diapers are described in U.S. Pat. No. 4,798,603 issued Jan. 17, 1989 to Meyer et al.; U.S. Pat. No. 5,176,668 issued Jan. 5, 1993 to Bernardin; U.S. Pat. No. 5,192,606 issued Mar. 9, 1993 to Proxmire et al., and U.S. Pat. No. 5,509,915 issued Apr. 23, 1996 to Hanson et al., the disclosures of which are herein incorporated by reference. The various aspects and configurations of the invention can provide distinctive combinations of softness, body conformity, reduced red-marking of the wearer's skin, reduced skin hydration, improved containment of body exudates and improved aesthetics.

The various components of the diaper 20 are integrally assembled together employing various types of suitable attachment means, such as adhesive, sonic and thermal bonds or combinations thereof. In the shown embodiment, for example, the outer cover 42 and bodyside liner 44 are assembled to each other and to the absorbent core 28 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Alternatively, the absorbent core 28 may be connected to the outer cover 42 using conventional fasteners such as buttons, hook and loop type fasteners, adhesive tape fasteners, and the like. The other components of the diaper 20 may be suitably connected together using similar means. Similarly, other diaper components, such as the elastic members 54 and 58 and the fasteners 60, may be assembled into the diaper 20 article by employing the above-identified attachment mechanisms. Desirably, the majority of the diaper 20 components are assembled together using ultrasonic bonding techniques for reduced manufacturing cost.

The outer cover 42 of the diaper 20, as representatively illustrated in FIG. 1, may suitably be composed of a material which is either liquid permeable or liquid impermeable. It is generally preferred that the outer cover 42 be formed from a material which is substantially impermeable to liquids. A typical outer cover 42 can be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). If it is desired to present the outer cover 42 with a more cloth-like feeling, the outer cover 42 may comprise a polyolefin film having a nonwoven web laminated to the exterior surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers. The polypropylene fibers have a thickness of about 1.5 to 2.5 denier per filament, which nonwoven web has a basis weight of about 17 grams per square meter (0.5 ounce per square yard). The outer cover 42 may otherwise include bicomponent fibers such as polyethylene/polypropylene bicomponent fibers. Methods of forming such cloth-like outer covers are known to those skilled in the art.

Further, the outer cover 42 may be formed of a woven or nonwoven fibrous web layer which has been totally or partially constructed or treated to impart a desired level of liquid impermeability to selected regions that are adjacent or proximate the absorbent core 28. Still further, the outer cover 42 may optionally be composed of a micro-porous "breathable" material which permits vapors to escape from the absorbent core 28 while still preventing liquid exudates from passing through the outer cover 42. For example, the outer cover 42 may include a vapor permeable non-woven facing layer laminated to a micro-porous film. Suitable "breathable" outer cover materials are described in U.S. Pat. No. 5,695,868 issued Dec. 9, 1997 to McCormack et al. and U.S. Pat. No. 5,843,056 issued Dec. 1, 1998 to Good et al., the descriptions of which are hereby incorporated by reference. Still further, the outer cover 42 may also be an elastomeric material such as a stretch-thermal laminate (STL), neck-bonded laminate (NBL), or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent No. 0217032 B1 issued on Feb. 19, 1992 to Taylor et al., the disclosures of which are hereby incorporated by reference. The outer cover 42 can also be embossed or otherwise provided with a matte finish to provide a more aesthetically pleasing appearance. The outer cover 42 may also contain discrete fastener elements 82 embedded therein as representatively illustrated in FIGS. 8 and 10.

The bodyside liner 44, as representatively illustrated in FIG. 1, suitably presents a bodyfacing surface which is compliant, soft feeling, and nonirritating to the wearer's skin. Further, the bodyside liner 44 may be less hydrophilic than the absorbent core 28, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent core 28.

Various woven and nonwoven fabrics can be used for the bodyside liner 44. For example, the bodyside liner 44 may be composed of a meltblown or spunbonded web of polyolefin fibers. The bodyside liner 44 may also be a bonded-carded web composed of natural and/or synthetic fibers. The bodyside liner 44 may be composed of a substantially hydrophobic material, and the hydrophobic material may optionally be treated with a surfactant or otherwise processed to impart a desired level of wearability and hydrophilicity. In a particular embodiment of the present invention, the bodyside liner 44 comprises a nonwoven, spunbond, polypropylene fabric composed of about 2.8-3.2 denier fibers formed into a web having a basis weight of about 20 grams per square meter and a density of about 0.13 grams per cubic centimeter. The fabric may be surface treated with about 0.3 weight percent of a surfactant commercially available from Hodgson Textile Chemicals, Inc. under the trade designation AHCOVEL Base N-62. The surfactant may be applied by any conventional means, such as spraying, printing, brush coating or the like. The surfactant may be applied to the entire bodyside liner 44 or may be selectively applied to particular sections of the bodyside liner 44, such as the medial section along the longitudinal centerline of the diaper 20, to provide greater wearability of such sections. The bodyside liner 44 may further include a composition applied thereto that is configured be transferred to the wearer's skin for improving the skin health of the wearer. Suitable compositions for use on the bodyside liner 44 are described in U.S. Pat. No. 6,149,934 issued Nov. 21, 2000 to Krzysik et al., the disclosure of which is hereby incorporated by reference. The bodyside liner 44 may also contain discrete fastener elements 82 embedded therein as representatively illustrated in FIG. 7.

The absorbent core 28 of the diaper 20, as representatively illustrated in FIG. 1, may suitably include a matrix of hydrophilic fibers, such as a web of cellulosic fluff, mixed with particles of a high-absorbency material commonly known as superabsorbent material. In a particular aspect, the absorbent core 28 includes a matrix of cellulosic fluff such as wood pulp fluff and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent core 28 to better contain and absorb body exudates. The concentration of the superabsorbent particles may also vary through the thickness of the absorbent core 28. Alternatively, the absorbent core 28 may include a laminate of fibrous webs and superabsorbent material or other suitable means of maintaining a superabsorbent material in a localized area.

The absorbent core 28 may have any of a number of shapes. For example, the absorbent core 28 may be rectangular, I-shaped, or T-shaped. It is generally preferred that the absorbent core 28 be narrow in the crotch region 26 of the diaper 20. It has been found that the absorbent core 28 of the present invention is particularly useful when the width dimension in the crotch region 26 is from about 2.5 to about 12.7 centimeters (1.0 to about 5.0 inches), desirably no more than about 7.6 centimeters (3.0 inches) and more desirably no more than about 5.1 centimeters (2.0 inches). The narrow crotch width dimension of the absorbent core 28 allows the absorbent core 28 to better fit between the legs of the wearer. The size and the absorbent capacity of the absorbent core 28 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core 28 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va., DOW DRYTECH 2035LD polymer available from Dow Chemical Co. located in Midland, Mich. and Stockhausen W65431 polymer available from Stockhausen Inc., located in Greensboro, N.C.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent core 28 in an amount of from about 5 to about 90 weight percent based on total weight of the absorbent core 28.

Optionally, a substantially hydrophilic tissue wrapsheet 112 may be employed to help maintain the integrity of the airlaid fibrous structure of the absorbent core 28. The tissue wrapsheet 112 is typically placed about the absorbent core 28 over at least the two major facing surfaces thereof and composed of an absorbent cellulosic material, such as creped wadding or a high wet-strength tissue. In one aspect of the invention, the tissue wrapsheet 112 can be configured to provide a wicking layer which helps to rapidly distribute liquid over the mass of absorbent fibers comprising the absorbent core 28. The wrapsheet material 112 on one side of the absorbent fibrous mass may be bonded to the wrapsheet 112 located on the opposite side of the fibrous mass to effectively entrap the absorbent core 28. A surge or fluid acquisition layer 50 may also be optionally included in order to provide improved distribution of fluid insults in a more uniform fashion over the absorbent core 28.

The disposable diaper 20 may include a pair of containment flaps (not illustrated) that are configured to provide a barrier to the lateral flow of body exudates. The containment flaps may be located along the laterally opposed side edges 30 of the diaper 20 adjacent the side edges 30 of the absorbent core 28. Each containment flap typically defines an unattached edge which is configured to maintain an upright, perpendicular configuration in at least the crotch region 26 of the diaper 20 to form a seal against the wearer's body. The containment flaps may extend longitudinally along the entire length of the absorbent core 28 or may only extend partially along the length of the absorbent core 28. When the containment flaps are shorter in length than the absorbent core 28, the containment flaps can be selectively positioned anywhere along the side edges 30 of diaper 20 in the crotch region 26. In a particular aspect of the invention, the containment flaps extend along the entire length of the absorbent core 28 to better contain the body exudates.

Such containment flaps are generally well known to those skilled in the art. For example, suitable constructions and arrangements for containment flaps are described in U.S. Pat. No. 4,704,116 issued Nov. 3, 1987, to K. Enloe, the disclosure of which is hereby incorporated by reference in a manner that is consistent (not contradictory) herewith.

The diaper 20 may further include elastics at the waist edges 32 and side edges 30 of the diaper 20 to further prevent leakage of body exudates and support the absorbent core 28. For example, as representatively illustrated in FIG. 1, the diaper 20 of the present invention may include a pair of leg elastic members 54 which are connected to the laterally opposed side edges 30 of the diaper 20 in the crotch region 26. The diaper 20 may also include a pair of waist elastic members 58 which are connected to the longitudinally opposed waist edges 32 of the diaper 20. The leg elastics 54 and waist elastics 58 are generally adapted to fit about the legs and waist of a wearer in use to maintain a positive, contacting relationship with the wearer to effectively reduce or eliminate the leakage of body exudates from the diaper 20.

Materials suitable for use as the leg elastics 54 and waist elastics 58 are well known to those skilled in the art. Exemplary of such materials are sheets or strands or ribbons of a polymeric, elastomeric material which are adhered to the outer cover 42 in a stretched position, or which are attached to the outer cover 42 while the outer cover 42 is pleated, such that elastic constrictive forces are imparted to the outer cover 42. The leg elastics 54 may also include such materials as polyurethane, synthetic and natural rubber.

The disposable diaper 20 may have tension around the waist of the user and tension around the leg of the user when initially donned. The mechanical fastening system of the present invention helps maintain the initial fastened position of the diaper 20 during use so as to maintain proper tension and ultimately proper fit. Referring to FIG. 4, tension around the waist and legs may be lost due to radial shifting and shear slippage of the mechanical fasteners 60 relative to the landing zone 80. Radial shifting occurs primarily in the direction indicated by arrows 96, whereas shear slippage occurs primarily in the direction indicated by arrows 98. The shear forces in the direction indicated by arrows 98 act to pull the fastening system apart in a direction essentially planer to the mechanical fastener 60 and the landing zone 80 and are imparted primarily by the flexible layer 62, the waist elastic 58, or the user's movements, or combinations thereof. The radial forces in the direction indicated by arrow 96 result primarily from the leg elastic 54, or the user's movements, or combinations of both. The fastening material 66 engages the base material 83 of the landing zone 80 to provide the primary resistance to shear forces and radial forces in the fastener overlap region 104. The discrete fastener elements 82 of landing zone 80 act to increase the coefficient of friction in the fastener overlap region 104 and reduce radial shifting and shear slippage. The discrete fastener elements 82 may be in contact with fastening material 66, flexible layer 62, the liner 44, or combinations thereof when the diaper 20 is fastened. Therefore, the interaction between the discrete fastener elements 82 and the flexible layer 62 and/or the liner 44 creates a secondary resistance to shear forces and radial forces during use.

This invention is further illustrated by the following examples, which are not intended to limit the scope of the invention. The following test materials and test methods used to evaluate individual samples of discrete fastener elements of the present invention are set forth below.

Test Methods

Coefficient of Friction

The following test was performed to determine the coefficient of friction between two materials. The procedure determines the sustained sliding (kinetic) friction of a material when sliding over another material. The coefficient of friction can be determined using ASTM method D 1894-99 with the following particulars.

A sled, which had the test specimen attached thereto, was pulled over a moving platen (table) that had another testing material attached thereto. The test specimen and material on the platen were in surface-to-surface contact with each other. "Coefficient of friction" is defined as the measure of the relative difficulty when the surface of one material slides over an adjoining surface of either itself or of another material. "STATIC" coefficient of friction is described as the highest instantaneous value obtained to begin movement between the surfaces. "KINETIC" coefficient of friction is the average of the values obtained during the 60 seconds of the test (6 inch travel distance).

The testing apparatus used was a LAB MASTER Slip and Friction Model 32-90 with a model number 32-90-06 test sled; both of which are available from Testing Machines, Inc. of Islanda, N.Y. 11722. This apparatus was equipped with a digital display, and the apparatus automatically calculated and displayed the kinetic coefficient of friction. The sled used for the testing had a weight of 100 grams. Testing occurred in a room having a temperature of between about 22 degrees Celsius and about 24 degrees Celsius, and at a relatively humidity of about 50%.

The test material mounted to the platen preferably has a length of about 305 millimeters and a width of about 102-127 millimeters. The test material can be mounted to the platen (table) using a contact adhesive or double-sided tape. The test material mounted to the sled preferably has a length of about 100 millimeters and a width of about 63 millimeters. The test material is mounted to the sled using a contact adhesive or double-sided tape.

The sled is positioned very lightly and gently on the surface of the moving platen to prevent any unnatural bond from developing. The length of the sled, the length of the connecting wire, and the length dimension of the plane-mounted material are parallel. The moving platen is then put in motion at a velocity of 6 inches per minute. After movement of the platen removes slack from a connecting wire to a Chatillon DFI gate, the gauge takes readings and continues to do so for about 60 seconds (6 inches of travel). The gauge measures and stores the "STATIC" value for the highest instantaneous coefficient of friction value obtained to begin the movement between the surfaces within the first inch of pull. The "KINETIC" value obtained and stored is the average of the values obtained during the 60 seconds of the test (6 inch travel distance).

The calculation for "KINETIC" coefficient of friction is obtained by the gauge using the following equation. $\mu k=Ak/B$, where $\mu k$=the kinetic coefficient of friction value, Ak=the average gram value obtained during the 60 second test period, and B=sled weight of about 100 grams. The calculation for "STATIC" coefficient of friction is obtained by the gauge using the following equation. $\mu s=As/B$, where $\mu s$=the static coefficient of friction value, As=the maximum initial gram value obtained within the first inch of pull, and B=sled weight of about 100 grams.

Shear Test

This test is used to measure the dynamic shear strength of two materials in face to face contact using a tensile tester. The two materials are engaged with a mechanical roller. Shear strength is achieved by pulling the two materials apart parallel to their plane of contact. The shear strength test values are an indication of how well the two materials stay engaged against in-plane shear force. Shear strength is the maximum force reached when a load is applied at a constant rate in a direction parallel to the direction of the interface between the two materials until separation occurs.

The tensile tester should be capable of obtaining a peak load and be equipped with an appropriate load cell. A suitable tensile testing system is a Model 2 Materials Test System Sintech Tensile Tester, commercially available from MTS Sintech, Research Triangle Park, N.C. Forced engagement of the two materials is achieved with a roll down machine including a rubber covered roller weighing 4.5 pounds, commercially available from Chemsultants International Network, Mentor, Ohio, under the part number RD-1000.

Figure 6:
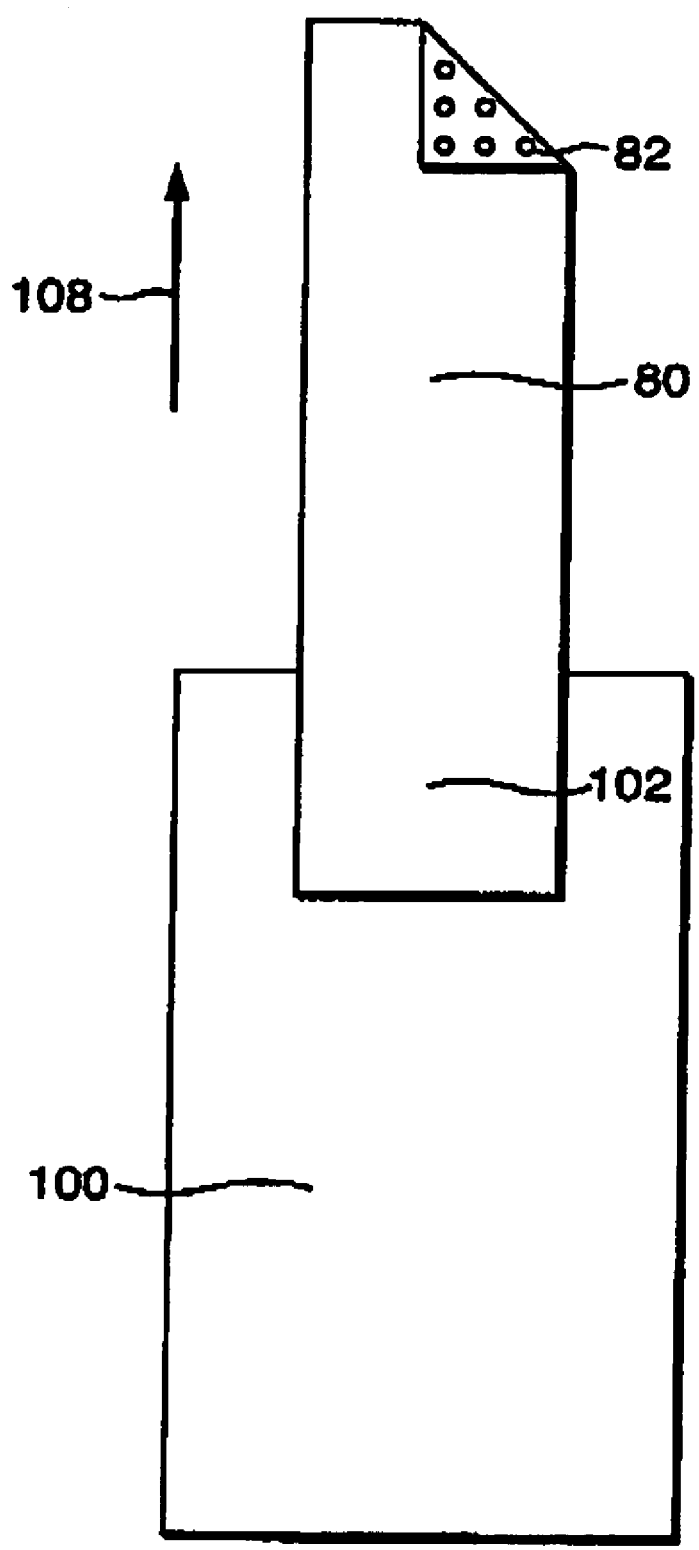
FIG. 6 representatively shows the sample orientation used to measure shear force.

The test samples were prepared by cutting the landing zone material 80, including discrete fastener elements 82, into one inch by four inch pieces. The opposing material 100 was cut into two inch by four inch pieces. As illustrated in FIG. 6, the landing zone material 80 was centered on one narrow end of the opposing material 100 with one inch of overlap between the two materials. The materials were positioned such that the side of landing zone material 80 with the discrete fastener elements 82 was in contact with the opposing material 100. This resulted in a 1 inch by 1 inch area of contact 102 between the two materials. The materials were engaged by force using the roll down machine. The 4.5 pound (2 kg) roller travels over the sample one time forward and one time backward at a rate of 60 inches/min (150 cm/min).

After the sample is prepared, the sample is inserted into the tensile tester. The jaws of the tester are initially set 3±0.04 inches (75±1 mm) apart. The tester is programmed to travel at a rate of 250 millimeters per minute (10 in/min). The crosshead is started in motion in a direction indicated by arrow 106 in FIG. 6. The peak load is recorded and the shear strength is determined by dividing the peak load by the area of contact between the two samples.

Materials

Sample A is a pattern-unbonded nonwoven fabric having continuous bonded areas defining a plurality of discrete unbonded areas as described in U.S. Pat. No. 5,858,515 issued to Stokes et al. on Jan. 12, 1999. The fibers or filaments within the discrete unbonded areas are dimensionally stabilized by the continuous bonded area that encircle or surround each unbonded area. The spaces between the fibers or filaments within the unbonded area remain sufficiently open or large to receive and engage hook elements. The nonwoven is a two layered material wherein the bottom layer is made of very fine strands of polypropylene fibers randomly formed. Each fiber of the top layer is about 50% polypropylene and about 50% random copolymer. The basis weight of sample A is about 1.5 ounces per square yard.

Sample B is a pattern-unbonded nonwoven as described in Sample A with the addition of discrete fastener elements 82 embedded in the nonwoven base material 83 in a linear pattern oriented in the fastener lateral direction 136. The discrete fastener elements 82 are spaced across the fastener longitudinal direction 134 such that there are about 3 lines of discrete fastener elements 82 per inch of nonwoven base material 83. Each discrete fastener element 82 is approximately 1400 microns wide. There are approximately 3-4 rows of protrusions 84 across the width of each discrete fastener element 82. The protrusions 84 are slightly cone shaped with a mostly flat upper surface 85 as representatively illustrated in FIG. 12. The protrusions 84 are approximately 300 microns in height and are approximately 100-120 microns wide on the mostly flat upper surface 85. The discrete fastener elements 82 and protrusions 84 are for the most part below the surface of the topography of the unbonded area of the nonwoven base material 83.

Sample C is a necked spunbond nonwoven material and is made from polypropylene with a fiber size of approximately 2 to about 2.5 denier, having a basis weight of approximately 0.6 ounce per square yard after necking the web to about 55% of it's original width.

Sample D is a polypropylene necked spunbond laminate, the spunbond layers having a basis weight of about 0.85 ounces per square yard after necking the web to about 40% of it's original width, and a fiber size of about 2 to about 2.5 denier, the necked spunbond laminate includes a Kraton G 2755 elastomeric film core with a basis weight of about 42 gsm extrusion coated between and in surface to surface relationship with the spunbond layers.

Sample E has a highly bonded polypropylene nonwoven base material 83 and generally circular-shaped discrete fastener elements 82 embedded therein. The discrete fastener elements 82 are also made of a polypropylene resin. Each circular discrete fastener element 82 is approximately 2000 microns in diameter and includes 12-16 protrusions 84. There are approximately 25 discrete fastener elements 82 per square inch of base material 83. The protrusions 84 are slightly cone-shaped with some of the protrusions 84 having flattened upper surfaces 85 and some having rounded upper surfaces 85, as representatively illustrated in FIGS. 11 and 15 respectively. Each protrusion 84 is approximately 250-350 microns in height and the flattened upper surface 85 is approximately 150-250 microns wide.

Sample F has a highly bonded polypropylene nonwoven base material 83 and generally circular-shaped discrete fastener elements 82 embedded therein. The discrete fastener elements 82 are also made of a polypropylene resin. Each circular discrete fastener element 82 is approximately 2000 microns in diameter and includes 16-22 protrusions 84. There are approximately 24 discrete fastener elements 82 per square inch of base material 83. The protrusions 84 are slightly cone-shaped and most have rounded upper surfaces 85, as representatively illustrated in FIG. 15. Each protrusion 84 is approximately 300-400 microns in height and the rounded upper surface 85 is approximately 125-175 microns wide.

Sample G is a point bonded nonwoven with discrete fastener elements 82 embedded in the nonwoven base material 83 in a linear pattern oriented in the fastener lateral direction 136. The discrete fastener elements 82 are spaced across the fastener longitudinal direction 134 such that there are about 5 lines of discrete fastener elements 82 per inch of nonwoven base material 83. Each discrete fastener element 82 is approximately 2000 microns wide. There are generally 4 rows of protrusions 84 across the width of each discrete fastener element 82 and there are approximately 4000 protrusions 84 per square centimeter of discrete fastener element 82. The protrusions 84 are cone-shaped with a mostly round upper surface 85 as representatively illustrated in FIG. 15. The protrusions 84 are approximately 375-400 microns in height and are approximately 100-150 microns wide at the upper surface 85.

Sample H has a highly bonded polypropylene nonwoven base material 83 and generally circular-shaped discrete fastener elements 82 embedded therein. The discrete fastener elements 82 are also made of a polypropylene resin. Each circular discrete fastener element 82 is approximately 5 millimeters in diameter and includes approximately 32 protrusions 84. There are approximately 9 discrete fastener elements 82 per square inch of base material 83. The protrusions 84 are slightly cone-shaped and most have rounded upper surfaces 85. As representatively illustrated in FIG. 13, each protrusion 84 forms less than a 90° angle with the garment facing surface 86 of the discrete fastener element 82. The protrusions 84 alternate such that each consecutive protrusion 84 points in the opposite direction than the previous protrusion 84. The protrusions 84 are approximately 640 microns in height and the rounded upper surface 85 is approximately 240 microns wide.

Sample I has a highly bonded polypropylene nonwoven base material 83 and generally circular-shaped discrete fastener elements 82 embedded therein. The discrete fastener elements 82 are also made of a polypropylene resin. Each circular discrete fastener element 82 is approximately 5 millimeters in diameter and includes approximately 32 protrusions 84. There are approximately 9 discrete fastener elements 82 per square inch of base material 83. The protrusions 84 are slightly cone-shaped and most have flat upper surfaces 85 as representatively illustrated in FIG. 11. As representatively illustrated in FIG. 13, each protrusion 84 forms less than a 90° angle with the garment facing surface 86 of the discrete fastener element 82. The protrusions 84 alternate such that each consecutive protrusion 84 points in the opposite direction than the previous protrusion 84. The protrusions 84 are approximately 400 microns in height and the flat upper surface 85 is approximately 250 microns wide.

Sample J has a highly bonded polypropylene nonwoven base material 83 and generally circular-shaped discrete fastener elements 82 embedded therein. The discrete fastener elements 82 are also made of a polypropylene resin. Each circular discrete fastener element 82 is approximately 5 millimeters in diameter and includes approximately 32 protrusions 84. There are approximately 9 discrete fastener elements 82 per square inch of base material 83. The protrusions 84 are mostly pushed down into the discrete fastener element 82 and are essentially blob-shaped as representatively illustrated in FIG. 14. The protrusions 84 are approximately 50-200 microns in height, approximately 600 microns in length, and approximately 300 microns in width.

Sample K has a highly bonded polypropylene nonwoven base material 83 and generally circular-shaped discrete fastener elements 82 embedded therein. The discrete fastener elements 82 are also made of a polypropylene resin. Each circular discrete fastener element 82 is approximately 2 millimeters in diameter. There are approximately 25 discrete fastener elements 82 per square inch of base material 83.

Sample L is a point bonded nonwoven with discrete fastener elements 82 embedded in the nonwoven base material 83 in a linear pattern oriented in the fastener lateral direction 136. The discrete fastener elements 82 are spaced across the fastener longitudinal direction 134 such that there are about 4 lines of discrete fastener elements 82 per inch of nonwoven base material 83. Each discrete fastener element 82 is approximately 1600 microns wide. There are generally 2 rows of protrusions 84 across the width of each discrete fastener element 82 and there are approximately 400 protrusions 84 per square centimeter of discrete fastener element 82. The protrusions 84 are cone-shaped with a mostly round upper surface 85 as representatively illustrated in FIG. 15. As representatively illustrated in FIG. 13, each protrusion 84 forms less than a 90° angle with the garment facing surface 86 of the discrete fastener element 82. The protrusions 84 alternate such that each consecutive protrusion 84 points in the opposite direction than the previous protrusion 84. The protrusions 84 are approximately 550 microns in height and are approximately 250 microns wide at the upper surface 85.

Sample M is a point bonded nonwoven with discrete fastener elements 82 embedded in the nonwoven base material 83 in a linear pattern oriented in the fastener lateral direction 136. The discrete fastener elements 82 are spaced across the fastener longitudinal direction 134 such that there are about 5 lines of discrete fastener elements 82 per inch of nonwoven base material 83. Each discrete fastener element 82 is approximately 2000 microns wide. There are generally 2-3 rows of protrusions 84 across the width of each discrete fastener element 82 and there are approximately 300 protrusions 84 per square centimeter of discrete fastener element 82. The protrusions 84 are cone-shaped with a mostly flat upper surface 85 as representatively illustrated in FIG. 12. As representatively illustrated in FIG. 13, each protrusion 84 forms less than a 90° angle with the garment facing surface 86 of the discrete fastener element 82. The protrusions 84 alternate such that each consecutive protrusion 84 points in the opposite direction than the previous protrusion 84. The protrusions 84 are approximately 400 microns in height and are approximately 200 microns wide at the upper surface 85.

EXAMPLES

The materials described above are representative of possible materials that could be found in fastening system of absorbent articles. Sample A is a pattern-unbonded nonwoven that may be used as base material 83 of a landing zone 80 that is one element of a hook and loop fastening system. Sample C is a necked spunbond nonwoven that may be used as a liner material 44 on the interior surface 34 of a diaper 20. Sample D is a necked spunbond laminate that may be used as the flexible layer 62 of mechanical fastener 60. Samples B, E, F, G, H, I, J, K, L, and M are material variations that may be used as landing zone 80 of the present invention. The discrete fastener elements 82, the base material 83, and the protrusions 84 are varied to illustrate the effect each has on the coefficient of friction and shear force in the overlap region 104 created when back waist region 24 overlaps the front waist region 22.

Referring to Table 1 below, the discrete fastener elements 82 and protrusions 84 of Sample B increase the force needed to drag it across Sample D or Sample C as compared to Sample A without the protrusions 84 or discrete fastener elements 82. This suggests that replacing Sample A with Sample B as the landing zone 80 would increase the coefficient of friction (COF) and reduce radial shifting in the overlap region 104 in the front waist region 22 of the absorbent article 20 making it less likely that the front waist region 22 would droop, or sag during use relative to the back waist region 24. It is expected that a different pattern of discrete fastener elements 82 used on the base material 83 of Sample A could increase resistance to radial shifting, or sliding, even more than the Sample B execution. For example, Sample E showed higher COF values than Sample B as well as a shear value (Table 2) and would be expected to further reduce radial shifting during wear. One concern that must be addressed when materials with increased shear values are employed in designs of this type is the possibility of skin irritation if the material contacts the skin of the wearer. It might be necessary to find a material with high COF and no shear when contact with the wearer's skin is anticipated. While this invention does not identify a material like this, it is known that certain polymers mentioned in this invention could provide the high COF values without shear. Rubbery polymers such as styrene isoprenes, butadienes, etc. are examples.

Samples E, H, L and M all exhibit higher COF values than Sample B and would also be expected to reduce droop and sag in the front waist region 22 at least as well, or better than Sample B.

Referring to Table 2 below, Sample E has higher shear engagement with Sample A, Sample D and Sample C making it more resistant to torsion forces and more suitable for use in an absorbent article, like a baby diaper 20. Samples E, H, I, L and M all increase shear force relative to Samples A, D, and C and would be more effective than Sample B in resisting drooping or radial shifting in the front waist region 22 of an absorbent article 20.

Sample M exhibits increased shear engagement with Sample A, but with much lower engagement to Sample D and almost no shear engagement to Sample C. This type of discrete fastener element would be expected to reduce the droop and sag of an absorbent material where the front waist area employs a Sample A material, or a Sample A like material, but it would be expected to do much less to prevent droop, or sagging if employed in the area where it would be expected to work with Sample D or Sample C type material. Sample M type discrete fastener elements would not be a good choice in a FIG. 8 type execution, but it could be an excellent choice in a FIG. 7 execution where the front waist area is to be Sample A, or a material like Sample A.

TABLE 1

Coefficient of Friction

| Sample | Opposing Material on Table COF (std) | | |
|---|---|---|---|
| | A | D | C |
| A | Not tested | 0.719 (0.047) | 0.551 (0.028) |
| B | Not tested | 1.308 (0.077) | 0.958 (0.072) |
| E | 4.44 (0.09) | 4.04 (1.29) | 3.68 (0.74) |
| H | 2.16 (0.42) | 3.08 (0.38) | 1.96 (0.08) |
| L | 3.24 (0.85) | 4.38 (0.20) | 1.55 (0.47) |
| M | 6.85 (1.82) | 7.41 (1.40) | 4.57 (0.70) |

TABLE 2

Shear Force

| Sample | Opposing Material $g/in^2$ (std) | | |
|---|---|---|---|
| | A | D | C |
| E | 270 (100) | 240 (140) | 160 (70) |
| F | bdl* | bdl* | bdl* |
| G | bdl* | bdl* | bdl* |
| H | 120 (50) | bdl* | bdl* |
| I | 180 (105) | 50 (20) | 145 (50) |
| J | bdl* | bdl* | bdl* |
| K | bdl* | bdl* | bdl* |
| L | 200 (55) | 50 (40) | 230 (50) |
| M | 260 (115) | 50 (35) | bdl* |

*Below detectable level

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A disposable absorbent article comprising:
   a. an outer cover;
   b. a bodyside liner;
   c. a front waist region wherein the front waist region includes a pair of front ear portions;
   d. a back waist region wherein the back waist region includes a pair of back ear portions, and wherein the back ear portions include a mechanical fastener;
   e. a crotch region connecting the front waist region and the back waist region; and
   f. a first discrete fastener element group embedded in the outer cover in the front waist region, wherein the first discrete fastener element group includes a plurality of first discrete fastener elements, wherein the plurality of first discrete fastener elements have a profile height and the outer cover has a profile height and the profile height of the first discrete fastener elements is lower than the profile height of the outer cover, the first discrete fastener elements comprising a thermoplastic polymer and being semi-spherical with a circular cross-sectional shape or being generally linear with a rectangular cross-sectional shape, the first discrete fastener elements further comprising a garment facing surface and at least one protrusion extending from the garment facing surface.

2. The disposable absorbent article of claim 1 wherein the front ear portions further include a second discrete fastener element group embedded in the outer cover and the second discrete fastener element group includes at least one second discrete fastener element.

3. The disposable absorbent article of claim 2 wherein the second discrete fastener element has a cross-sectional shape and the first discrete fastener element has a different cross-sectional shape.

4. The disposable absorbent article of claim 2 wherein the back ear portions further include a third discrete fastener element group and the third discrete fastener element group includes at least one third discrete fastener element.

5. The disposable absorbent article of claim 4 wherein the third discrete fastener element group is embedded in the liner.

6. The disposable absorbent article of claim 4 wherein the mechanical fastener further includes a flexible layer and a fastening material and wherein the third discrete fastener element group is embedded in the flexible layer.

7. The disposable absorbent article of claim 6 wherein the back ear portions further include a fourth discrete fastener element group embedded in the liner and wherein the fourth discrete fastener element group includes at least one fourth discrete fastener element.

8. The disposable absorbent article of claim 1 wherein the back ear portions further include a second discrete fastener element group and the second discrete fastener element group includes at least one second discrete fastener element.

9. The disposable absorbent article of claim 8 wherein the second discrete fastener element group is embedded in the liner.

10. The disposable absorbent article of claim 8 wherein the mechanical fastener further includes a flexible layer and a fastening material and wherein the second discrete fastener element group is embedded in the flexible layer.

11. The disposable absorbent article of claim 10 wherein the back ear portions further include a third discrete fastener element group embedded in the liner and wherein the third discrete fastener element group includes at least one third discrete fastener element.

* * * * *